(12) United States Patent
Fulton, III

(10) Patent No.: US 9,277,935 B2
(45) Date of Patent: Mar. 8, 2016

(54) TEMPORARY VASCULAR SCAFFOLD AND SCORING DEVICE

(71) Applicant: Nfinium Vascular Technologies, LLC, Grand Junction, CO (US)

(72) Inventor: Richard Eustis Fulton, III, Grand Junction, CO (US)

(73) Assignee: Quadra Endovascular, Inc., Grand Junction, CO (US)

( * ) Notice: Subject to any disclaimer, the term of this patent is extended or adjusted under 35 U.S.C. 154(b) by 0 days.

(21) Appl. No.: 14/080,917

(22) Filed: Nov. 15, 2013

(65) Prior Publication Data

US 2014/0142598 A1    May 22, 2014

Related U.S. Application Data

(60) Provisional application No. 61/796,596, filed on Nov. 15, 2012.

(51) Int. Cl.
*A61B 17/3207* (2006.01)
*A61F 2/82* (2013.01)
(Continued)

(52) U.S. Cl.
CPC ....... *A61B 17/320725* (2013.01); *A61B 17/221* (2013.01); *A61F 2/82* (2013.01); *A61B 2017/22061* (2013.01); *A61B 2017/22084* (2013.01)

(58) Field of Classification Search
CPC ............... A61B 17/320725; A61B 17/221; A61B 2017/22084; A61B 2017/22061; A61B 17/32075; A61B 17/320758; A61B 17/32002; A61B 17/320016; A61B 2002/8483; A61B 2002/8486; A61B 2002/9505; A61B 2002/9511; A61B 2002/9522; A61B 2002/9583; A61B 2002/9586; A61B 2002/9665; A61B 2/95; A61B 2/962; A61B 2/966; A61B 2/97; A61F 2/82; A61F 2/848; A61F 2/86; A61F 2/88; A61F 2/885; A61F 2/90; A61F 2/958
USPC .............. 623/1.11–1.18, 1.22, 1.42; 606/108, 606/159, 198, 200
See application file for complete search history.

(56) References Cited

U.S. PATENT DOCUMENTS

| 5,059,178 A | 10/1991 | Ya |
| 5,449,372 A | 9/1995 | Schmaltz et al. |

(Continued)

OTHER PUBLICATIONS

International search report and written opinion dated Feb. 14, 2014 for PCT/US2013/070440.

(Continued)

*Primary Examiner* — Jonathan W Miles
*Assistant Examiner* — Lucas Paez
(74) *Attorney, Agent, or Firm* — Wilson, Sonsini, Goodrich & Rosati

(57) ABSTRACT

Devices and methods for treating a target site in a body lumen are provided. A medical device includes a stent-like structure including a plurality of scoring and non-scoring filaments interwoven with one another. Generally, the stent-like structure will have more non-scoring filaments than scoring filaments to provide greater structural support and to focus the scoring forces on only a few select areas. The stent-like structure is expanded within the target site to score the target site and to provide temporary structural support while the target site is infused with a therapeutic agent. Such therapeutic agent infusion occurs with the use of a drug eluting or drug coated balloon disposed within the stent-like structure or by occluding the target site and introducing a drug into the occluded target site to sit for a period of time.

35 Claims, 15 Drawing Sheets

(51) Int. Cl.
*A61B 17/221* (2006.01)
*A61B 17/22* (2006.01)

(56) References Cited

U.S. PATENT DOCUMENTS

| | | | |
|---|---|---|---|
| 5,766,203 A | 6/1998 | Imran et al. | |
| 5,797,935 A | 8/1998 | Barath | |
| 5,879,380 A | 3/1999 | Kalmann et al. | |
| 6,022,336 A | 2/2000 | Zadno-Azizi et al. | |
| 6,142,987 A * | 11/2000 | Tsugita | 604/500 |
| 6,221,006 B1 | 4/2001 | Dubrul et al. | |
| 6,450,989 B2 | 9/2002 | Dubrul et al. | |
| 6,537,195 B2 * | 3/2003 | Forman | 600/3 |
| 6,652,505 B1 | 11/2003 | Tsugita | |
| 6,733,519 B2 | 5/2004 | Lashinski et al. | |
| 6,808,531 B2 | 10/2004 | Lafontaine et al. | |
| 6,887,266 B2 * | 5/2005 | Williams et al. | 623/1.16 |
| 7,011,654 B2 | 3/2006 | Dubrul et al. | |
| 7,232,432 B2 | 6/2007 | Fulton, III et al. | |
| 7,279,002 B2 | 10/2007 | Shaw et al. | |
| 7,494,497 B2 | 2/2009 | Weber | |
| 7,909,810 B2 * | 3/2011 | Noone | 604/509 |
| 8,454,636 B2 | 6/2013 | Konstantino et al. | |
| 2003/0220683 A1 * | 11/2003 | Minasian et al. | 623/1.15 |
| 2004/0138738 A1 | 7/2004 | Stinson | |
| 2005/0080478 A1 | 4/2005 | Barongan | |
| 2005/0163954 A1 | 7/2005 | Shaw | |
| 2006/0184191 A1 * | 8/2006 | O'Brien | 606/192 |
| 2006/0259005 A1 * | 11/2006 | Konstantino et al. | 604/500 |
| 2009/0105687 A1 * | 4/2009 | Deckman et al. | 604/509 |
| 2011/0040319 A1 | 2/2011 | Fulton, III | |
| 2011/0082483 A1 * | 4/2011 | Diamant et al. | 606/159 |
| 2013/0041391 A1 * | 2/2013 | Spencer et al. | 606/159 |
| 2013/0297003 A1 * | 11/2013 | Pinchuk | 623/1.12 |

OTHER PUBLICATIONS

Tepe, et al. Local delivery of paclitaxel to inhibit restenosis during angioplasty of the leg. N Engl J Med. Feb. 14, 2008;358(7):689-99. doi: 10.1056/NEJMoa0706356.

* cited by examiner

TEMPORARY VASCULAR SCAFFOLD AND SCORING DEVICE

CROSS-REFERENCE TO OTHER APPLICATIONS

This application claims the benefit of U.S. Provisional Application No. 61/796,596, filed Nov. 15, 2012, which application is incorporated herein by reference.

This application is related to co-pending and co-owned U.S. patent application Ser. No. 12/813,339 filed on Jun. 10, 2010, which claims the benefit of U.S. Provisional Application No. 61/274,165 filed on Aug. 13, 2009 and U.S. provisional application No. 61/277,154 filed on Sep. 21, 2009, the disclosures of which are incorporated by reference.

This application is also related to co-owned U.S. Pat. No. 6,238,412, the disclosure of which is incorporated by reference.

BACKGROUND OF THE INVENTION

Balloon angioplasty has been a popular method of treating vascular occlusions since 1976. With plain old balloon angioplasty (POBA), there exists a significant subset of patients who have immediate suboptimal results related to the trauma to the vessel including dissection of the vessel, incomplete plaque compression, poor lumen gain, and acute elastic recoil of the vessel, amongst others. Because of these suboptimal immediate results, other means to treat vascular stenosis were developed. Intravascular stents are widely utilized, addressing the acute problems of angioplasty and reducing the restenosis rates from 50-60% for POBA to 30-35% for these bare metal stents (BMS).

Because the restenosis rates of BMS are usually unacceptable, drug eluting stents (DES) are used to inhibit restenosis. These devices reduce the restenosis rate to around 20% and lower in the coronary circulation. However, DES are extremely expensive and can lead to thrombosis, which can prove fatal. In addition, DES are not particularly effective in the peripheral circulation. The expense of drug eluting stents at over $3000 each dramatically increases the overall cost of healthcare in the U.S. Finally, not only are the stents are costly, but expensive and potentially harmful drugs are routinely used for at least a year after stent implantation.

Restenosis is an Achilles heel of all vascular intervention, from angioplasty to stenting and even surgery. Various drugs can prevent restenosis. A primary question is how best to deliver the drugs in the most cost effective manner available while producing good patient outcomes and preventing complications.

Because of variable plaque morphology and composition, stresses provided by conventional POBA can be unpredictable, and frequently high pressure balloon inflations are often needed to successfully provide enough stress to crack the plaque. When the plaque does compress at high pressures, the balloon will often very rapidly expand to its full dimension in a noticeable pop (tenths of a second), very rapidly expanding the vessel wall often rupturing the smooth muscle cells. Dissection frequently occurs, as does irreparable injury to the smooth muscle cells which do not have the chance to gradually stretch and deform to maintain their integrity.

Therefore, methods and devices that lower the pressure at which the plaque will fracture will often produce a slower and more gradual stretching of the arterial wall. This slower stretching can diminish the degree of trauma to the vessel.

A wire or wires along the outside of an angioplasty balloon, sometimes called buddy wires, can produce focal areas of stresses along the wires that were approximately 120 times that of a conventional balloon surface, and the stress patterns from the external wire extends into the plaque rather than being concentrated on the surface as with a conventional balloon. The stress patterns are typically less dependent on the morphology and composition of the plaque than with conventional balloons. In other words, the stresses can be more predictable and concentrated and require lower balloon pressures to compress the plaque. Clinical studies have confirmed that when compared to conventional POBA catheters, the buddy wire technique compressed the plaque at lower balloon pressures, caused fewer dissections, had less elastic recoil, and had more lumen gain, as well as a trend toward lower restenosis rate.

More recently, cutting and scoring balloons have been introduced extending these concepts. One such balloon uses several razor type blades along the balloon margins. Scoring balloons may utilize several 0.005 to 0.007 inch struts placed over a balloon. Both balloon types are commercially successful. They are typically used in treating complex lesions or in plaque modification. The scoring balloon has been shown to achieve 50% more lumen gain than POBA when utilized as predilatation before stent implantation. This procedure can significantly reduce the number of dissections when compared to POBA. The scoring balloon also has been shown to not slip off of the lesion, which is a problem with POBA. The scoring balloon can also be more effective in soft, fibrous, and calcified plaques than POBA and has been recommended as a strategy of plaque modification in treating complex lesions. The use of the scoring balloon has thus resulted in very low incidences of inadvertent or unplanned stenting, commonly referred to as bail out stenting.

Prolonged inflation times improve the immediate results of POBA with fewer dissections, fewer further interventions such as stenting, and less restenosis. On the other hand, other studies did not show improvement in long term results with prolonged inflation times, possibly because their prolonged inflations were the result of treating dissections. Currently, no studies that evaluate both plaque modification and prolonged inflation times have been conducted or published.

While these mechanical strategies have resulted in measurable improvement in the acute complications of POBA, a promising advancement in POBA has been the advent of drug eluting balloons (DEB's). A DEB is a POBA balloon coated with an antiproliferative drug, such as paclitaxel. The drug is delivered during the rather short balloon inflation and has been shown to be present in smooth muscle cells up to six days later. The drug from a DEB covers essentially 100% of the plaque/vessel wall vs. only 15-20% with drug eluting stents. Compared to DES in treating coronary in-stent restenosis, a DEB seems preferable. In the THUNDER trial (sponsored by University Hospital Tuebingen, Tuebingen, Germany, reported in The New England Journal of Medicine, volume 358:689-699, Feb. 14, 2008, Number 7), a DEB was compared to POBA in the peripheral vasculature. DEB was very effective, and at 2 years, the target lesion revascularization rate was only 15% with the DEB vs. 59% with POBA. Most experts in the field expect the general usage results of DEB's in coronary circulation to be in the range of drug eluting stents, i.e., a restenosis rate of around 20% or so. This rate leaves considerable room for improvement.

Therefore, both mechanical and pharmacological strategies have shown advantages in treating vascular lesions with balloon angioplasty. The mechanical strategies effectively address the acute or immediate problems by causing less injury to the vessel and the pharmacological strategy of drug eluting balloons significantly diminish restenosis.

Moreover, recent experiments have demonstrated that infusion of paclitaxel, an antiproliferative drug, directly into the artery may be just as effective as drug eluting balloons or drug eluting stents. This is usually done by employing a catheter specifically designed for infusion of a drug over the site of the angioplasty or stent placement after the angioplasty and/or stent placement. This type of catheter usually has two balloons, one proximal and one distal. The drug or other agent is infused between the two in a closed system, drug infusion performed after the angioplasty, stent placement or other therapeutic procedure. This typically requires removal of the angioplasty balloon or stent delivery catheter, which is utilized prior to the drug delivery, and subsequent placement of a separate device to deliver the drug. This can be problematic not only because of the cost of the extra device, but also because platelets adhere over the fissures in the plaque and about the small areas of injury in the arterial wall while the exchange is taking place, preventing some of the drug from being delivered to the wall where it is needed. Additionally, by just infusing a drug into a space that has been previously dilated, there is very little pressure forcing the drug into the wall. Subsequent to the therapeutic procedure and the drug delivery steps, the drug is then released downstream.

In U.S. Pat. No. 5,059,178, Ya et al. describe a device with a downstream balloon catheter blocking element and an upstream suction catheter with a balloon blocking element for the removal of thrombus from a blood vessel. The device is utilized to dissolve the thrombus by injecting a dissolving agent into the space between the two balloons and then withdraw the dissolved thrombus from the body through upstream suction catheter. Any subsequent intervention or therapy (angioplasty, stent placement, and the like) are performed after the removal of the dissolved thrombus.

In U.S. Pat. No. 6,022,366, Zadno-Azizi et al. describe another double balloon device similar to one described by Ya above but is directed toward embolic containment. This device is actually a three catheter irrigation/aspiration system and also has an innermost downstream balloon blocking or occluding element and an outermost upstream balloon occlusion catheter with an intermediate catheter between the two. The irrigation/aspiration of debris and emboli occurs by use of the outer pathway between the upstream balloon occlusion catheter and the intermediate catheter, and by the use of the inner pathway between the intermediate catheter and the innermost downstream balloon blocking element. The use of three catheters tends to reduce the cross-sectional size of the pathway available for aspiration of material.

In U.S. Pat. No. 5,449,372, Schmalz et al. describe a temporary stent that can be used for support after dilatation of the lesion.

In U.S. Pat. Nos. 6,450,989 and 7,011,654, William R. Dubrul and I describe a dilating and support apparatus with disease inhibitors and methods of use.

In U.S. Pat. No. 7,232,432, William R. Dubrul and I describe a porous braided structure for angioplasty and drug delivery.

The following U.S. Patents and Publications may also be of interest: U.S. Pat. Nos. 8,454,636, 7,494,497, 7,279,002, 6,808,531, 5,797,935, and 5,766,203, and U.S. Publication Nos. 2013/0041391, 2011/0082483, and 2005/0080478.

BRIEF SUMMARY OF THE INVENTION

To address the problem of how best to deliver the drugs in the most cost effective manner available while producing good patient outcomes and preventing complications, the medical device industry has essentially focused on developing methods and devices that inhibit the vascular response to the injury (restenosis), as opposed to developing a device that causes less injury, and hence less restenosis. One aspect of the present invention is directed to a device and method that both causes less injury to the vasculature by the use of dilatation of a specialized braid over a balloon causing less dissection and more even plaque disruption at lower pressures and introduces drug deep within the vessel wall; this latter act is accomplished by using proximal and distal occluders, injecting an agent, such as an anti-proliferative drug, into the region between the occluders, and performing an intervention, such as balloon angioplasty, while the occluders and injected agent remain in place. Another aspect of the invention also helps to maintain pressure upon the vessel wall similar to prolonged balloon inflation by using a braided, stent like structure as a temporary or transient stent. Thus less initial injury and less elastic recoil should result in less restenosis, and delivering a drug will further reduce or prevent the restenosis.

It is the immediate result of an intervention (the immediate lumen diameter and the immediate residual percent stenosis) that typically determines the late outcome after coronary or other vascular intervention. Many embodiments of the present invention are designed to improve these two factors. An optimal outcome in percutaneous interventions depend upon: 1) obtaining an excellent acute angiographic results with less dissection and elastic recoil, 2) avoiding damage to the distal vascular bed (as with atherectomy), and 3) reducing smooth muscle cell proliferation with pharmacological intervention. Aspects of the present invention address all three areas.

Many embodiments of the present invention are directed to a method of treating a target site within a vascular channel of the body using a catheter assembly, the catheter assembly comprising a proximal occluder and a distal occluder. The method includes the following steps. The proximal occluder is positioned in a vascular channel-occluding state within the vascular channel at a first position proximal of a target site thereby occluding the vascular channel at the first position. The distal occluder is positioned in a vascular channel-occluding state within the vascular channel at a second position distal of a target site thereby occluding the vascular channel at the second position and thereby defining a region between the distal and proximal occluders. An agent is injected into the region. An intervention is performed at the target site while the distal and proximal occluders are in their vascular channel-occluding states and the agent is in the region. The catheter assembly is removed from the vascular channel.

In some embodiments, the intervention performing step comprises expanding an expansion device, such as a balloon and a temporary stent structure covering the balloon, against an inner wall of the vascular channel. In some embodiments, the balloon is collapsed leaving the stent structure expanded against the inner wall for a period of time, and the collapsed balloon and the collapsed stent structure are removed from the vascular channel during the stent structure removing step.

In many embodiments, the balloon stent assembly comprises a catheter assembly having a proximal portion and a distal portion. The catheter assembly may comprise first and second elongate members. A temporary stent may have proximal and distal ends; the proximal end being secured to a first position along the first elongate member and the distal end being secured to a second position along the second elongate member. The temporary stent may be placeable in a contracted state by movement of the first and second positions away from one another. The assembly may also include an inflatable balloon mounted to the distal portion of the catheter assembly at a location surrounded by the temporary stent. The balloon may be placeable in an inflated state, thereby placing the temporary stent in an expanded state, and in a collapsed state. The temporary stent can be free to remain in the expanded state when the balloon moves to the collapsed state.

By utilizing the balloon to expand the temporary stent, not only the pressure of the balloon is brought to bear on the obstruction, but its actions can be enhanced by the overlying temporary stent structure. The wires of the temporary stent may provide areas of focal force on the plaque that will allow the plaque or obstruction to be dilated with less pressure creating a controlled expansion compared to the uncontrolled rupture and dissections frequently seen with POBA. There may be a more gradual stretching and more gradual deforming of the smooth muscle cells, and they may have an opportunity to accommodate this stretching and maintain their integrity rather than being irreparably injured as is frequently the case with POBA.

Therefore, the balloon can serve two distinct functions: 1) it can dilate the plaque or obstruction (and in a more consistent manner because of the overlying temporary stent structure), and 2) it can dilate the temporary stent more effectively, with more force, and with more lumen gain than could be achieved by dilating the temporary stent structure without the assistance of the balloon.

Therefore, together the balloon along with the temporary stent may be able to effectively dilate and then support the dilated vessel subsequent to the dilatation.

In some embodiments, the first elongate member comprises an outer, actuator sleeve and the second elongate member comprises an inner, balloon catheter shaft to which the balloon is mounted. In some embodiments, the temporary stent comprises a porous braided stent structure.

Treating advanced vascular disease is one of the largest health care expenses born by society. There are projected to be one million non-coronary angioplasties and 900,000 stand alone coronary angioplasties in 2012. (Millennium Research Group, 2009. American Heart Association, Heart Disease and Stroke Statistics, 2009 Update at a Glance.) Many simpler, less expensive interventional methods, such as POBA, are frequently not effective, necessitating the use of more complex and expensive alternatives, such as stenting and surgery, which cost billions of dollars each year.

The use of the present invention is expected to improve on the results of POBA and reduce or avoid the need for stenting and/or surgery, by causing less vascular injury initially, preventing elastic recoil that frequently demands stenting, and preventing restenosis by simultaneously administering a non-proliferative agent. Procedures conducted according to many embodiments of the present invention are expected to cost only marginally more than POBA.

A rough calculation shows that the use of many embodiments of the present invention could result in large cost savings of over $1 billion per year as approximately 1.9 million peripheral angioplasties and stand alone coronary angioplasties (not associated with stent implantation) will be performed in 2012. (Millennium Research Group, 2009. American Heart Association, Heart Disease and Stroke Statistics, 2009 Update at a Glance.) By replacing POBA with the many embodiments of the present invention in all cases, and diminishing the re-intervention rate from 40% of 1.9 million patients (760,000 patients) to 10% (190,000 patients), approximately 570,000 patients would be spared re-intervention. At a Medicare reimbursement cost of $5850/procedure, there would be savings of $3.33 billion/year. Currently, such restenotic lesions are usually treated with stents, surgery, or other more costly methods. On average, these added procedures add a cost of about $2,000 for each procedure. If the $2000 is added to each re-intervention in 80% of these cases, then the savings are increased by $912 million (570,000 procedures×80%×$2000=$912 MM), for a total possible savings of $4.24 billion per year. A market penetration of 25% would result in yearly cost savings of over $1 billion per year, not even considering the expected diminished incidence of costly "bail out" or unanticipated stenting when using the present invention.

An aspect of the present invention provides a medical device for treating a target site in a body lumen. Often, the target site will be a region of a blood vessel occluded with plaque. The medical device may comprise a stent-like structure which may comprise a plurality of scoring filaments or elements and a plurality of non-scoring filaments or elements. The scoring filaments and the non-scoring filaments may be interwoven with one another. Alternatively or in combination, at least some of the scoring and non-scoring filaments may not be interwoven with one another. For example, the filaments may be struts of a laser-cut scaffold. The stent-like structure may typically comprise a tubular mesh braid. The plurality of non-scoring filaments may be configured to radially support the body lumen after the stent-like structure has been expanded therein. The stent-like structure may comprise more non-scoring filaments than scoring filaments. By providing more non-scoring filaments or elements than scoring filaments or elements, greater structural strength and improved scoring by the stent-like structure can be provided. Scoring of a lesion or occlusion in the body lumen, for example, may depend on providing a focal force at one or several areas upon and within the plaque. If too many filaments are scoring filaments, this focal force would be diluted or divided over all of the filaments and none may be dominant in directing force into the plaque to cause the plaque to fracture beneath the scoring filaments. Thus, only a limited number of scoring filaments or elements may be needed to produce the desired results of a few areas of focal fracturing of plaque present in the body lumen such as a blood vessel.

The stent-like structure typically has an expanded configuration and a collapsed configuration. The stent-like structure in the expanded configuration may be collapsible into the collapsed configuration. The stent-like structure in the expandable configuration can be collapsed into the collapsed configuration by axially shortening the stent-like structure.

One or more of the plurality of scoring filaments or the plurality of non-scoring filaments may be non-axial. For example, one or more of the plurality of scoring filaments or the plurality of non-scoring filaments may be helically wound over a longitudinal axis of the stent-like structure. Also, one or more of the plurality of scoring filaments or the plurality of non-scoring filaments may be helically wound in the same direction.

Each scoring filament may have one or more of a pointed, triangular, or rectangular shape. Each non-scoring filament may have one or more of a flat, rounded, rectangular, or cylindrical shape. At least one scoring filament may comprise a plurality of notches for receiving at least one non-scoring filament as the non-scoring filament(s) crosses through the scoring filament(s). The plurality of notches may be distributed (e.g., evenly distributed) over a length of the at least one scoring filament.

The medical device may further comprise an expandable element. The stent-like structure may be disposed over the expandable element. The expandable element may be expandable to urge the stent-like structure radially outward against an inner wall of the body lumen. The expandable element may comprise an inflatable balloon. The expandable element may be independently collapsible from the stent-like structure. The expandable element may comprise an outer surface coated with a therapeutic agent or substance. The expandable element may comprise one or more pores for releasing a therapeutic agent or substance.

The medical device may further comprise a catheter shaft, and the expandable element may be disposed over the catheter shaft. The medical device may further comprise an expandable proximal occluder disposed over the catheter shaft proximal of the expandable element and the stent-like structure. The medical device may further comprise an expandable distal occluder. The distal occluder may be advancable through an inner lumen of the catheter shaft to be positioned distal of the expandable element and the stent-like structure. The distal occluder may non-inflatable, for example, such as a malecot.

Another aspect of the present invention provides a medical device for treating a target site in a body lumen. Often, the target site will be a region of a blood vessel occluded with plaque. The medical device may comprise a stent-like structure which may comprise a plurality of scoring filaments and a plurality of non-scoring filaments. The scoring filaments and the non-scoring filaments may be interwoven with one another. Alternatively or in combination, at least some of the scoring and non-scoring filaments may not be interwoven with one another. At least one scoring filament may comprise a plurality of notches for receiving at least one non-scoring filament as the non-scoring filament(s) crosses through the scoring filament(s). The plurality of notches may be distributed (e.g., evenly distributed) over a length of the at least one scoring filament.

Another aspect of the present invention provides methods of treating a target region in a body lumen. Often, the target site will be a region of a blood vessel occluded with plaque. A catheter assembly may be positioned at or near a target region in the body lumen. An expandable element of the catheter assembly may be expanded (i) to expand a stent-like structure disposed over the expandable element and (ii) to urge both the expandable element and the stent-like structure against an inner wall of the target region. In some embodiments, the inner wall may also be scored with one or more of the stent-like structure or the expandable element. A therapeutic agent may be released from an outer surface of the expandable element for infusion into the inner wall. Alternatively or in combination, a therapeutic agent may be released from one or more pores of the expandable element for infusion into the inner wall. In many embodiments, the target region may be isolated by expanding at least two occluders—a distal occluder distal of the target region and a proximal occluder proximal of the target region. The expandable element may be collapsed to leave the stent-like structure expanded against and radially supporting the inner wall. The stent-like structure may be left expanded against the inner wall for a period of time to one or more of (i) inhibit elastic recoil of the inner wall, (ii) allow the therapeutic agent to infuse into the inner wall, and (iii) inhibit or minimize flow limiting dissections. Finally, the stent-like structure may be collapsed after the period of time and the catheter assembly may then be from the target region.

Other features, aspects and advantages of the present invention can be seen on review the figures the detailed description, and the claims which follow.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a mechanical schematic showing the device fully deployed in a Dacron® graft used in hemodialysis. FIG. 1 shows the blocking element at the distal end of the catheter in its radially expanded state and the occlusion engaging element at the distal end of the support wire in its radially expanded state. The proximal blocking element may take a variety of shapes as would be required for the particular application. The preferred shape is likely to be a funnel shape where the larger diameter is distal to the lesser diameter that is proximal on the element. This funnel shape can allow the obstruction to be more easily accepted into the catheter due to the pull/push of the engaging element, aspiration or both.

FIG. 2 is a side view of the distal portion of the support wire with a braided occlusion engaging element in its radial compressed state. FIG. 2 shows the state where the support wire and engaging element can be inserted through the occlusion that is to be removed.

FIG. 3 shows the FIG. 2 braided occlusion engaging element in its radially expanded state, which is the state shown in FIG. 1.

FIG. 4 is a perspective view, in partial cross-section, showing the multi-wing malecot type blocking element at the distal end of the catheter in its radially expanded state, which is the state shown in FIG. 1. It should be noted that the scale of the FIG. 4 catheter is much reduced compared to the scale of the occlusion removal wire and braided element shown in FIGS. 2 and 3.

FIG. 5 is a side view, in partial cross-section, showing the catheter and dilator with a ferrule at the distal tip of the guide wire in a passageway having an occlusion that is to be removed.

FIG. 6 is a side view, in partial cross-section, showing the next step in which the dilator is being removed thereby causing the malecot type blocking mechanism to become expanded by virtue of pressure against the distal end of the catheter tip of the dilator.

FIG. 7 is a side view, in partial cross-section, showing the next step in which the support wire together with the braided occlusion removal element in its radially compressed state (the state shown in FIG. 2) is inserted through the catheter and through the occlusion to be removed.

FIG. 8 is a side view, in partial cross-section, showing the next step in which the braided occlusion removal element has been expanded and is being pulled in a proximal direction thereby forcing the occlusion into the catheter for removal with or without aspiration.

FIG. 9 is a perspective view, in partial cross-section, showing the multi-wing malecot type blocking element at the distal end of the catheter in its radially expanded state.

FIG. 10 is a side view, in partial cross-section, showing the shape of the expansion resulting from the malecot type blocking element shown in FIG. 9.

FIG. 11 is a side view, in partial cross-sectional, view of a catheter assembly with the balloon expanded at a target site, in accordance with many embodiments.

FIGS. 12-17 are side views, in partial cross-section, showing the various steps in the use of the catheter assembly of FIG. 11.

FIGS. 18-20 show side views of another embodiment of a catheter assembly in which a removable, expandable braid, acting as a stent like structure, is positioned over the balloon, with the balloon and the braided stent-like structure both in expanded states in FIG. 18, with the braided stent like structure in an expanded state and the balloon in a collapsed state in FIG. 19, and the balloon and a braided stent like structure both an collapsed states in FIG. 20.

DETAILED DESCRIPTION OF THE INVENTION

Figure 1:
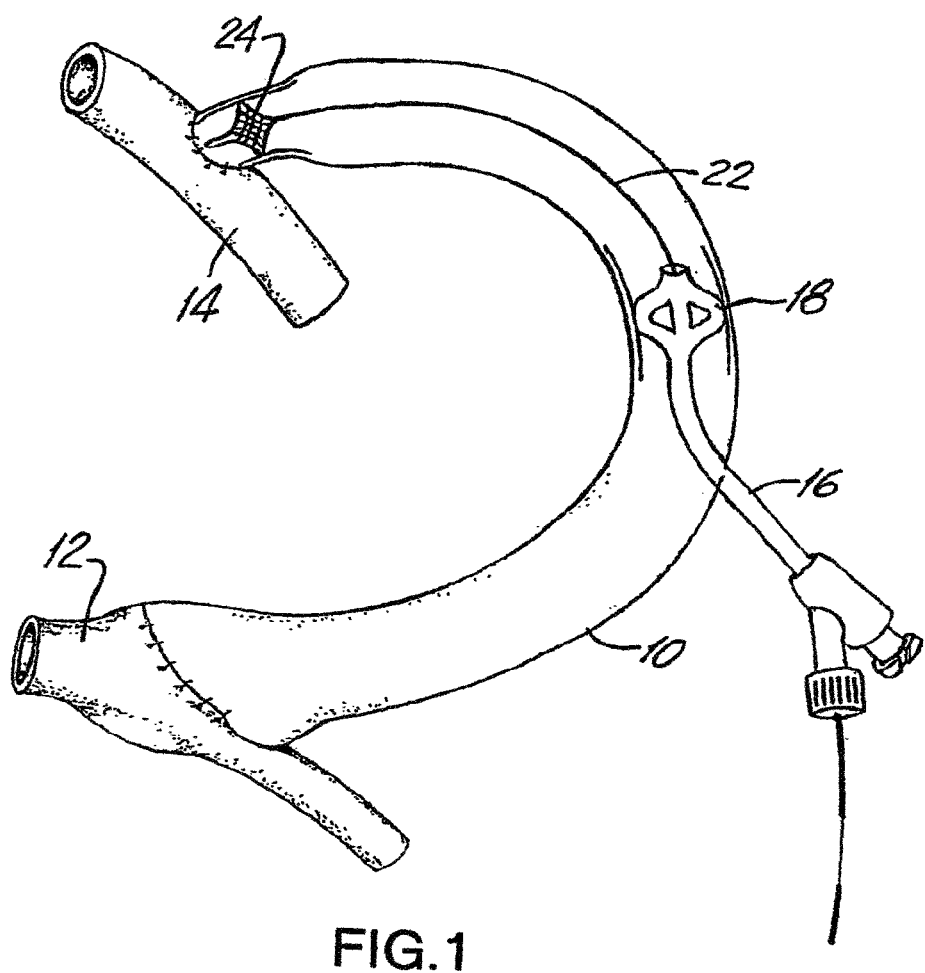
FIGS. 1-10 show structures as shown in co-owned U.S. Pat. No. 6,238,412.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

FIG. 1 shows a typical synthetic graft 10 used in hemodialysis. The graft extends between a vein 12 and an artery 14. The graft 10 may be about thirty centimeters long with an inner diameter (I.D.) of 6 or 7 millimeters. A catheter 16 can be inserted through the wall of the graft or vessel. Typically, the catheter might have an outside diameter (O.D.) of 2.7 mm and an inner diameter (I.D.) of 2.3 mm. A malecot type expansion device 18 may be covered with a membrane 20 (see FIG. 4). When expanded, it can serve to block the annular space between the outside wall of the catheter 16 and the graft 10. A support wire 22 for a braided removal mechanism 24 will typically have an outside diameter of about one mm and has an internal actuator rod 26 (see FIG. 2) of approximately 0.5 mm. Because of the simplicity of the design, this outside diameter could be smaller than 0.5 mm. In FIG. 1, the malecot type blocking device 18 and the braided removal device 24 are both shown in their expanded state and are positioned so that retrograde or proximal movement of the support wire 22 will pull the braided element in a proximal direction to push out whatever coagulated blood is between the braided device 18 and the distal end of the catheter into the catheter opening where it can be aspirated; thereby clearing the blockage in the graft or other vessel.

The structure of FIG. 1, which has been tested, was designed for use in a hemodialysis graft 10 having an I.D. of approximately six to seven mm. In the tested case, the catheter 16 has an 8 French O.D. (2.7 mm) and a 7 French I.D. (2.3 mm). The support wire 22 comprises a fairly standard movable core guide wire of 35 mils (that is, 0.35 inches, which is slightly under 1 mm). The actuator rod 26 in the support wire may be approximately 15 mils and thus slightly under 0.5 mm. The braided element 24 may have an insertion diameter that is approximately one mm and may expand to cover the seven mm diameter of the graft. In order to achieve this seven fold increase in diameter, the braided element can have a length of 11 to 13 mm. Thus, the catheter can have an annulus of about 2.3 mm around the support wire, through which annulus the blood occlusion is aspirated.

Figure 2:
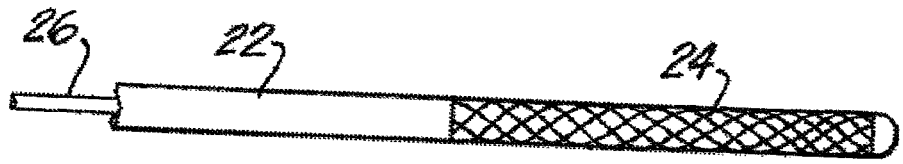
Figure 3:
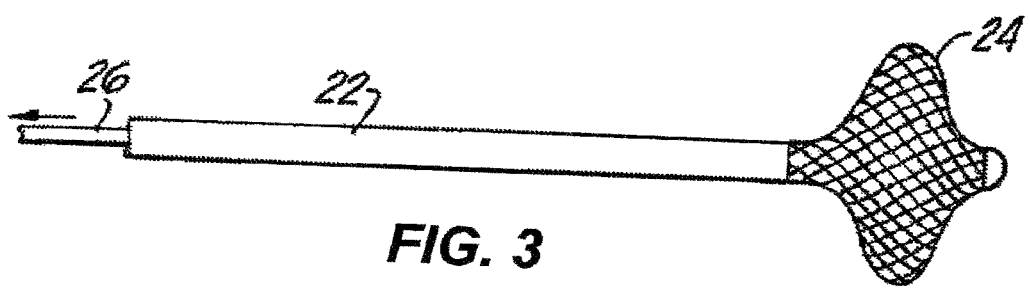

FIGS. 2 and 3 illustrate the support wire 22 and braided element 24 which constitute the occlusion engaging element that is moved proximal to push the occlusion into the catheter for removal. A preferred occlusion engaging element 24 may comprise a braided element. The braided material often has a stiffness such that it will not collapse or fold under the pressure of the occlusion when this engaging element is being moved proximally. Yet, the filaments that form the braid often must be flexible enough to be moved between the two states as shown in FIGS. 2 and 3. Materials from polyester to stainless steel can be successfully used.

The distal tip of the braided element 24 may be connected to the distal tip of the actuator rod 26. The proximal edge of the braided element 24 may be bonded to the distal end of the support wire 22. Thus, when the actuator rod 26 is pushed in a distal direction relative to the wire 22, the braided device can be forced into its collapsed state shown in FIG. 2 and is available to be pushed through the catheter and through or around the occlusion which is to be removed. When this engaging element 24 has been fully inserted, the actuator rod 26 may be moved in a proximal direction causing the braided element 24 to take the expanded position such as that shown in FIG. 3 so that subsequent movement of the entire support wire 22 can cause the braided element to move against the occlusion and push the occlusion into the distal end of the catheter. In some circumstances, the braided element 24 might be left as a braid with openings because the portions of the occlusion which may pass through the openings will be sufficiently smaller liquids so that they do not have to be removed. In other circumstances, it may be desirable to cover the braided element 24 with a membrane or film so that it becomes substantially impermeable. Further the membrane or film covering the engaging element will be helpful in preventing trauma to the inner walls of native tissue. Even further, this membrane may be helpful in optimizing the physical characteristics of the engaging element.

With reference to FIG. 1, it might be noted that when the braided element is pushed all the way down to one end of the graft 10, as shown in FIG. 1, and then expanded, the braided element will typically be expanding against a portion of the wall of the graft that is smaller than the bulk of the graft. However, as the support wire 22 is pulled to move the braided occlusion removal element proximally, the braided occlusion element can ride on the wall of the graft and can expand as the wall of the graft expands as long as tension is maintained on the actuator rod 26.

There might be applications in accordance with many embodiments of the present invention where the passageway involved is a tissue passageway such as a blood vessel or other channel within the body, where this braided element 24 is expanded to nearly the diameter of the vessel so that when it is moved to push out an occlusion, it will avoid trauma to the wall of the vessel. Further, the membrane on the expanding element will aid in decreasing the trauma to native vessels as described above. In such a case, the engaging element (and the blocking element) may be used only as a seal so that the obstruction may be removed or otherwise obliterated. This seal can allow the rest of the vessel to be uncontaminated and can provide for a closed system for irrigation and/or aspiration and subsequent obliteration or removal of the obstruction.

Figure 4:
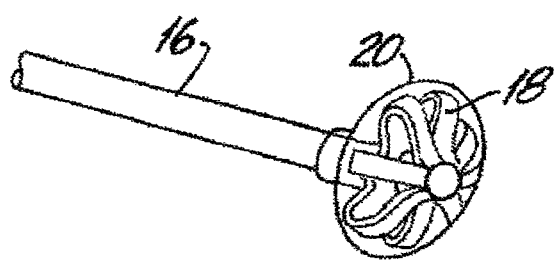
Figure 5:
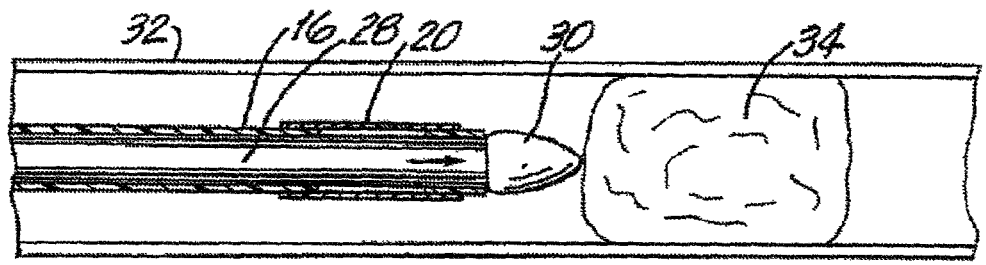

FIG. 4 illustrates the catheter 16 with the malecot 18 in an expanded state on the distal end of the catheter. A membrane 20 is normally used in order to provide a complete blocking or sealing function. Further, the membrane 20 may aid in locking the blocking element in a particular shape. This malecot type element can be created by making longitudinal slits in the sidewall of the catheter (or an attachment bonded thereto) thereby creating links or wings that will expand when the distal end of the catheter is pushed in a proximal direction. The appropriate pushing of the proximal end of the catheter can be achieved, as shown in FIG. 5, by a ferrule 30 which is a standard tip on a standard dilator 28. Alternatively or in combination, the dilator 28 may be a guide wire (which is usually much longer and flexible than a dilator) for remote obstruction removal. In such an application, the guide wire may have a ferrule type mechanism that may act like the ferrule on the dilator. In this instance, the guide wire (with ferrule) may be inserted into the vessel to the obstruction. The catheter may then be pushed along the guide wire until it reached the ferrule which would normally be located near the distal end of the guide wire. At this point, the wire may be pulled back, the ferrule may butt against the catheter and force out the blocking sealing element. The engaging element may be used with this blocking element and it could even be the ferruled wire as well.

It should be noted that the retention catheter described in U.S. Pat. No. 3,799,172 issued on Mar. 26, 1974 to Roman Szpur illustrates a structure that is similar to the malecot type device 18 illustrated in FIG. 4; although in that patent it is used as a retention device whereas here it is used as a blocking element.

This blocking element 18 is often called a malecot in the industry. It should be understood herein that the term malecot is generally used to refer in general to this type of multi-wing device.

Figure 6:
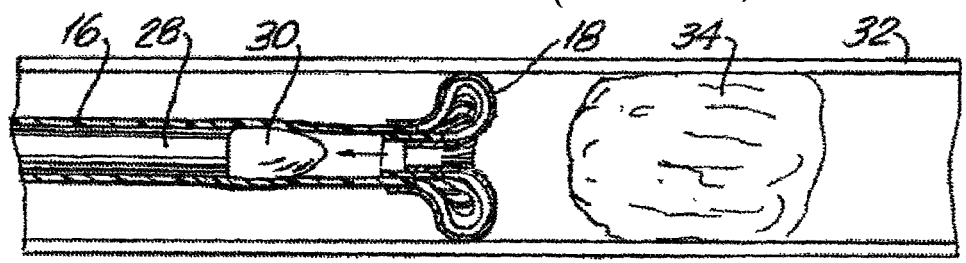

More specifically, as shown in FIG. 5, the catheter 16 together with a dilator 28 having an expanded tip 30, which is a ferrule, can be inserted into a vessel 32 such as the graft shown in FIG. 1. The catheter 16 and dilator 28 may be inserted close to the occlusion 34 and then the dilator 28 may be removed. Proximal motion of the dilator 28 may cause the tip 30 to contact the distal end of the catheter 16 forcing the distal end of the catheter to put pressure on the malecot wings creating the expansion shown in FIG. 6 (and also schematically shown in FIG. 1). Once this expansion has occurred, the dilator with its tip can be removed from the catheter (as shown in FIG. 6).

Figure 7:
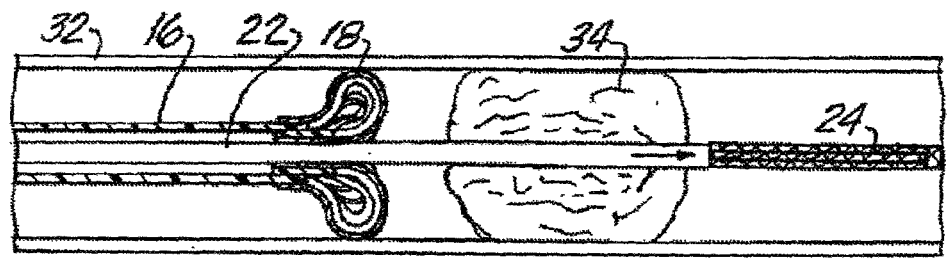
Figure 8:
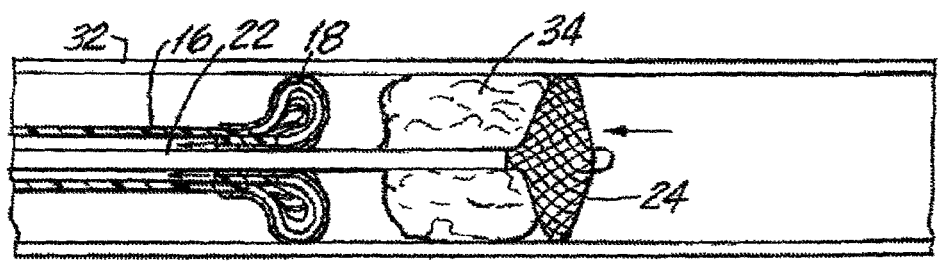

What then occurs is shown in FIGS. 7 and 8. As shown in FIG. 7, the support wire 22 with its braided removal element 24 may be inserted in the collapsed state so that it passes through or around the occlusion 34. It should be noted that the support wire 24 may be inserted prior to the blocking catheter being inserted or after the catheter is inserted (the latter of which is illustrated in the FIGS.). Most of the occlusions to which the device of FIGS. 1-8 is directed, such as congealed blood in a graft, will permit a support wire 22 to pass through it because the consistency is that of viscous material which can be readily penetrated. Alternatively, if the occlusion is a non viscous material such as a stone, plaque, emboli, foreign body, etc. the support wire 22 is small enough to be passed around the occlusion. Once the braided element 24 is on the distal side of the occlusion 34, the actuator rod 26 may be pulled, creating the expanded state for the braided device. Accordingly, distal movement of the entire support wire may cause the expanded braided device to move against the occlusion and force it into the catheter for removal with or without aspiration. When removal of obstructions that are located some distance away from the point of access into the body such as the carotid artery via a groin access the wire 22 would likely be inserted first. In this case, the support are 22 with its expanding element 24 may be used as a guide wire to guide the catheter to the preferred location. Of further import is that the blocking element and the engaging element may be used without any relative motion once deployed. Such is the case when irrigation and/or aspiration is used for the obstruction removal. In this case, the two elements can be used as seals against the tubular inner walls on both sides of the obstruction whereby the obstruction is removed from that sealed space with the use of aspiration, irrigation, or both. Further other means of obliterating the obstruction within this sealed space may be employed. Some of those means are, but are not limited to the addition of dissolving agents, delivery of energy such as ultrasound, laser or light energy, hydraulic energy and the like.

Other Comments

An important consideration of the device described herein is that the support wire with its expanding element can be fabricated with a very small diameter. This may be important because it allows an optimally large annular space between the wire and the inside of the catheter for maximum obstruction removal. Previous engaging elements have been used that use a balloon for the engaging element. This balloon design may require a larger shaft diameter than that of the presently described non-balloon designs according to many embodiments. Hence in these previous devices, the annular space is not maximized as in the presently described non-balloon embodiments. The term wire may be used to refer to the support portion of the removal device. The material of the wire need not necessarily be metal. Further, it may be desirable to use a 'double' engaging element (i.e. two braided or malecot expanding elements separated a distance appropriate to entrap the occlusion) in the case for example where the occlusion is desired to be trapped in the vessel. The term wire may be used herein to refer to a dual element device having a shell component and a core or mandril component which are longitudinally moveable relative to one another so as to be able to place the braided occlusion engaging element into its small diameter insertion state and its large diameter occlusion removal state.

Figure 9:
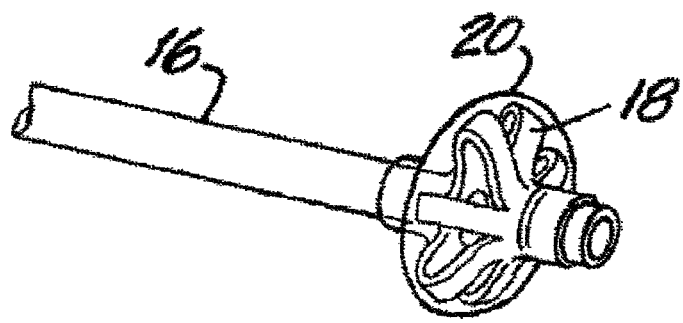
Figure 10:
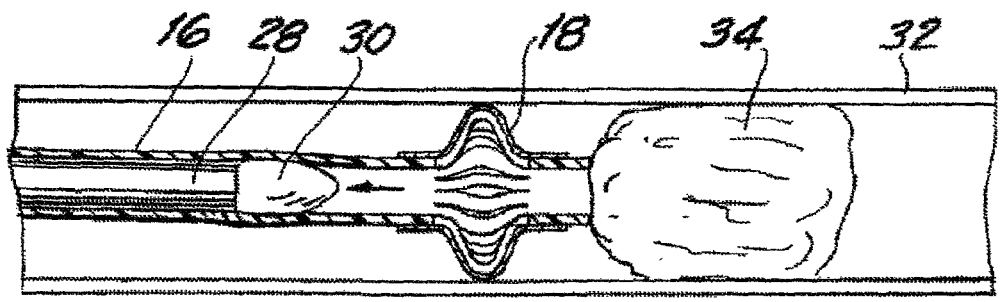

Although the blocking element is often described as a malecot type of device, it should be understood that the blocking element may be designed in various fashions which are known in the art. See, for example, FIGS. 9 and 10. As another example, an appropriately designed braid arrangement could be used as the blocking element. In that case, the catheter may have to be a dual wall catheter in which the inner and outer annular walls are able to move relative to one another in a longitudinal direction so as to place the braid used as a blocking element in its small diameter insertion state and its large diameter blocking state. Alternatively, it may be a single wall similar in design to the malecot style blocking element described previously.

It should be further understood that there might be a situation in which the blocking element or even the occlusion engaging element would be provided to the physician in a normal expanded state so that when the device is deployed, it would, through plastic memory or elastic memory, automatically snap into its expanded state.

Discussion of Method for Treating a Target Site in a Vascular Body Channel

The above-described structure and methods provide a good background for the following description of the presently claimed invention. Corresponding structures are referred to with corresponding reference numeral, such as support wire 22/support wire 122, and occlusion 34/occlusion 134.

Figure 11:
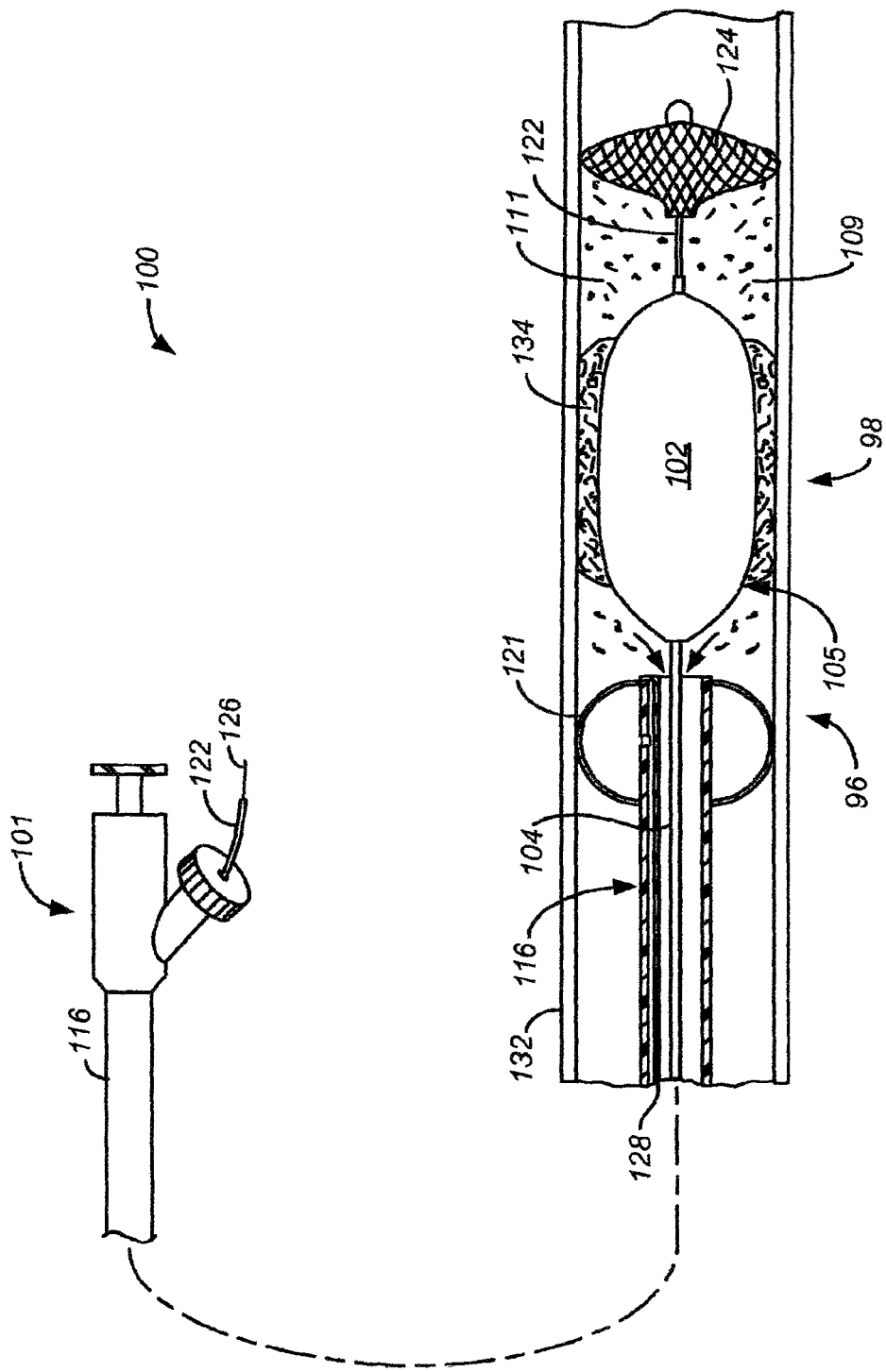
FIGS. 11-20 illustrate exemplary devices and procedures in accordance with many embodiments of the present invention.

FIG. 11 illustrates a catheter assembly 100 including a proximal end portion 101, from which proximal occluder catheter shaft 116 extends and passes into blood vessel 132, and a distal end portion 96 at a target site 98 within blood vessel 132. Distal occluder 124 is typically positioned at a location distal of target site 98 while balloon type proximal occluder 121 is typically positioned at a location proximal of the target site to define a region 109 therebetween. Occluders of types other than those illustrated as proximal and distal occluders 121, 124, such as malecot type occluders, can also be used. However, the annular balloon type of proximal occluder 121 illustrated may be preferred for its simplicity of construction and lower cost. Catheter assembly 100 also includes a balloon assembly 105 comprising a balloon catheter shaft 104 passing through proximal occluder catheter shaft 116 with a balloon 102 at its distal end. Support wire 122, with an actuator 126 passing therethrough, extends from distal occluder 124 and passes through balloon catheter shaft 104. Balloon 102 is shown in an expanded state pressing against occlusion 134. If desired, balloon 102 may comprise a drug eluting balloon. FIG. 11 also shows an injected agent 111 within region 109. Agent 111 may include various types of therapeutic and/or diagnostic agents, such as paclitaxel, sirolimus, other anti-proliferative drugs, contrast agent, thrombolytic agent, stem cells, agents to dissolve the obstruction, agents to change a vulnerable plaque to a non vulnerable plaque and the like. As discussed in more detail below, agent 111 acts on the occlusion 134 and the inside surface of a vessel 132 at the target site 98 during the intervention, in this example by balloon 102.

Figure 12:
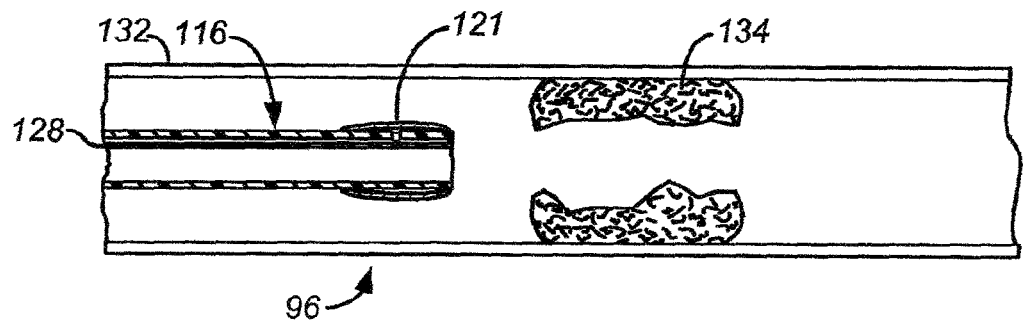
Figure 13:
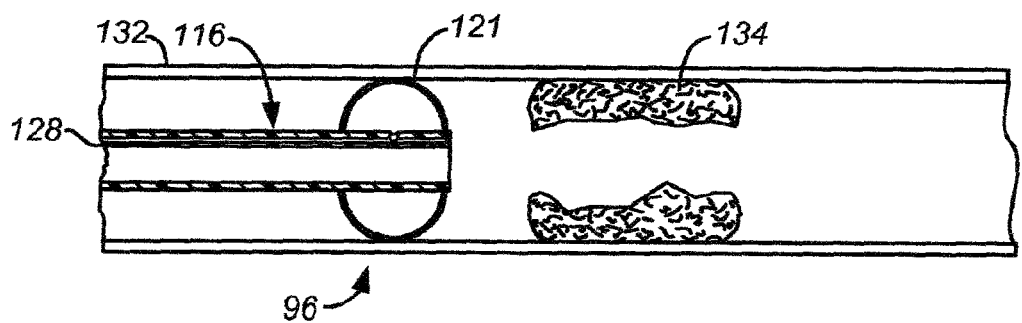
Figure 14:
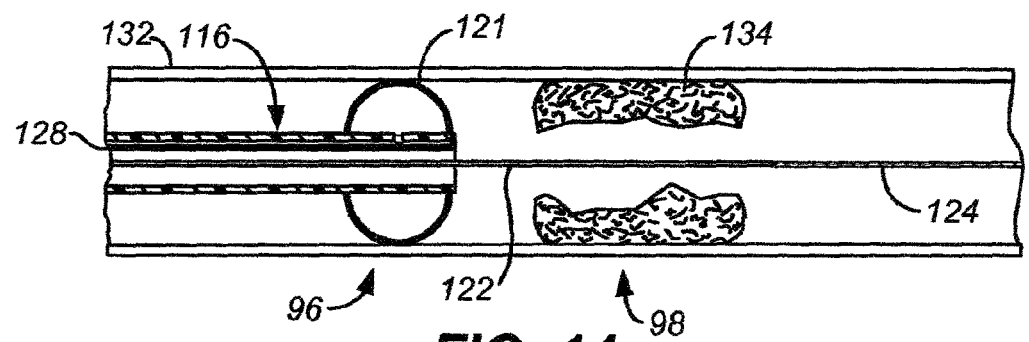
Figure 15:
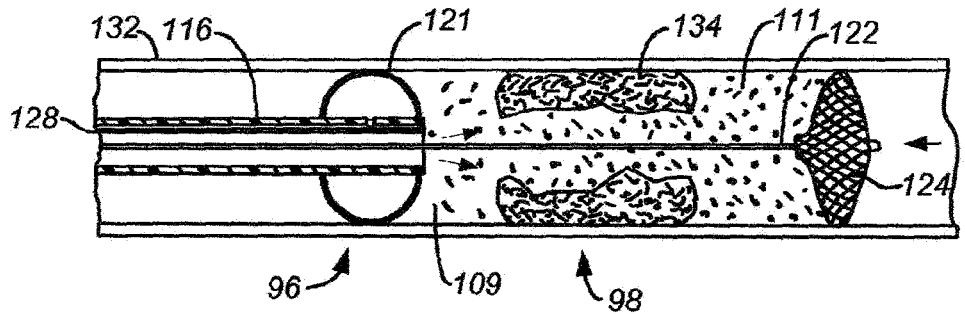
Figure 16:
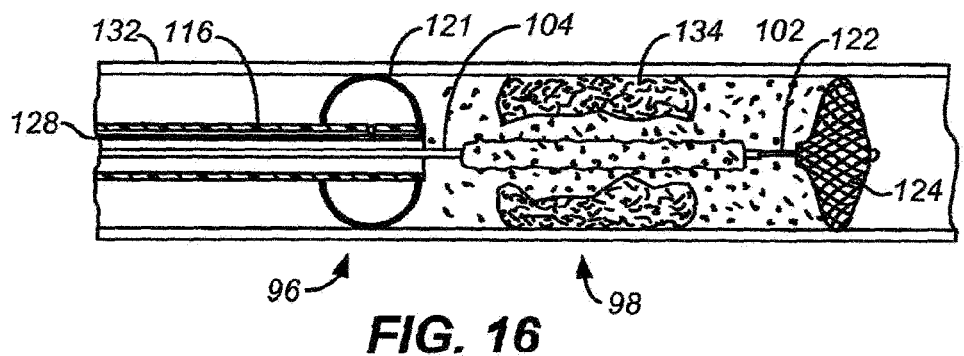
Figure 17:
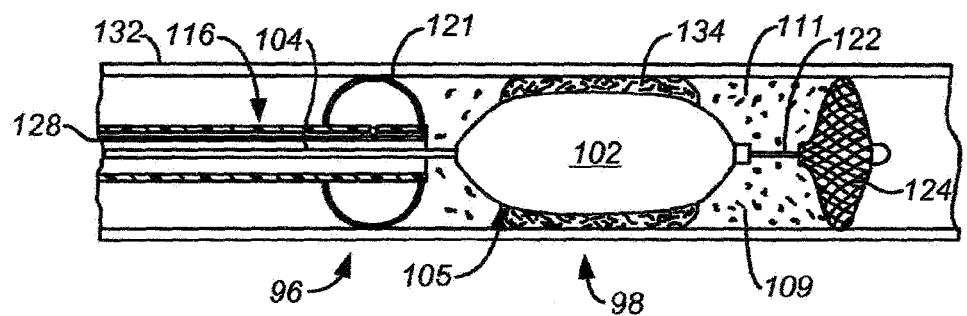

FIGS. 12-14 show the initial steps during the use of catheter assembly 100. These steps correspond to FIGS. 5-7, discussed above, with an exception that occlusion 134 does not totally block blood vessel 132. FIG. 15 is similar to FIG. 8 but also shows the introduction of injected agent 111 into region 109 between proximal occluder 121 and support wire 122. In some embodiments, the region 109 is aspirated through catheter shaft 116 prior to injecting agent 111. The use of proximal and distal occluders 121, 124 may concentrate agent 111 at and around occlusion 134 at target site 98. FIG. 16 also shows balloon catheter shaft 104, with a balloon 102 at its distal end, inserted over support wire 122 until balloon 102, in its deflated state, is positioned at occlusion 134. FIG. 17 shows balloon 102 expanded against occlusion 134. Balloon 102 can then be deflated, back to the state of FIG. 16, followed by the removal of balloon assembly 105 to the condition of FIG. 15. Region 109 can then be aspirated to remove material from the region; the aspiration may be in conjunction with pulling distal occluder 124 proximally at least part of the way towards proximal occluder 121 and/or partial collapse of distal occluder 124 to permit retrograde blood flow past the distal occluder 124 and into region 109. Alternatively, the contents of region 109 may be allowed to flow downstream as the total dose administered would likely not be harmful to the patient. After aspiration of region 109 is complete, distal occluder 124 can be collapsed to the condition of FIG. 14 and pulled back into catheter shaft 116. Proximal occluder 121 is collapsed by deflating balloon 102 through balloon catheter shaft 104.

The entire time balloon 102 is operating on occlusion 134, or some other intervention is being conducted at the target site 98, agent 111 may be present to bathe target site 98, including occlusion 134 and the inner wall of blood vessel 132 between occluders 121 and 124. This aspect of the invention may be highly important because both the intervention, such as with angioplasty balloon 102, and the injected agent therapy are conducted essentially simultaneously without the need for removal and replacement of catheters and interventional tools.

In some embodiments, proximal and distal occluders 121, and 124 are maintained in place to maintain agent 111 at target site 98 for a period of time, such as several minutes to hours, after balloon 102 has been collapsed. In some situations, more than one target site 98 may be treated through the placement of occluders 121, 124 in contracted states, moving the occluders to a new target site, re-expanding the occluders to their expanded states followed by injecting a agent 111 into the newly created region 109 and performing an intervention at the target site, typically using a balloon 102.

Ever since stents were introduced in the 1980's, investigators have searched for devices and methods to provide temporary support to the vascular wall without leaving a stent, which can never be removed, in the vessel forever. Bare metal stents have an unacceptable restenosis rates, and drug eluting stents, while having a moderately acceptable restenosis rate, are extremely expensive, have long term sequelae such as late stent thrombosis, and patients must stay on costly and potentially dangerous platelet inhibitor and other drugs for one year to life. Biodegradable and bioabsorbable stents have been proposed and produced, but they are less effective than either bare metal stents or drug eluting stents.

One particular use of devices according to many embodiments is to utilize part or all of the system before a bare metal stent (BMS) delivery. Drug eluting stents (DES) deliver the drug to only a small portion of the vessel wall that is stented because of the spaces between the drug eluting stent struts. Utilizing the current device with the agent injected into the closed space 109 before expansion of a BMS would bathe 100% of the vessel wall and still have the stent present to counteract elastic recoil, if it did occur, remodeling of the vessel, dissections, and other problems associated with vascular interventions. The BMS could be used with the proximal and distal occluders primarily. Alternatively, the temporary balloon stent apparatus could be utilized with the occluders and the agent between them as outlined below. If there was an unsatisfactory result after treatment with the entire system of occluders, agent, and temporary balloon stent, then the BMS may be deployed as a "bail-out" procedure. The agent may or may not be reapplied, having already been utilized before the aforementioned temporary stent application.

The prior art does not address a removable balloon stent apparatus that dilates the plaque and supports the wall after plaque dilatation. Lashinski et al. in U.S. Pat. No. 6,773,519 describe a stent like device which is deployed and then removed, and describes a removable coupler which is part of the device, but not a removable stent. Tsugita in U.S. Pat. No. 6,652,505 describes a guided filter which may be used to deliver a stent and removed, but not a removable stent. Kahmann in U.S. Pat. No. 5,879,380 describes a device and method for relining a section of blood vessel that has been injured or removed, not a device to both dilate the lesion and prevent elastic recoil as does the many embodiments of the present invention discussed below with reference to FIGS. 18-20.

Further embodiments of the present invention will be described with reference to FIGS. 18-20. This example is intended to dilate the occlusion 130 and inhibit elastic recoil by providing temporary stenting. Balloon assembly 140 includes balloon catheter shaft 104 with balloon 102 at its distal end and an actuator sleeve 144 surrounding balloon catheter shaft 104. A radially expandable braid 142 can be positioned over balloon 102. Balloon 102 and braid 142 are shown expanded in FIG. 18. The distal end 146 of braid 142 may be secured to the distal end of balloon catheter shaft 104 while the proximal end 148 of braid 142 may be secured to the distal end of actuator sleeve 144. Therefore, braid 142, although a stent like structure, comprises a nonremovable part of balloon assembly 140 and can be removed from the patient following the procedure.

Figure 19:
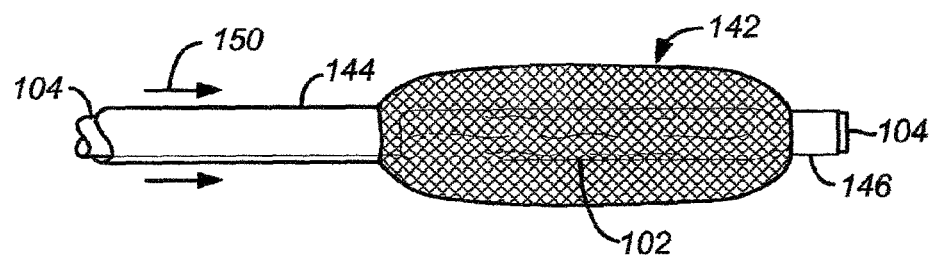

FIG. 19 shows balloon 102 in a collapsed state and that by moving the actuator sleeve 144 distally in the direction of arrows 150, the braid 142 may become expanded over the collapsed balloon 1, as shown in FIG. 19, and will stay expanded when balloon 102 is deflated and collapsed. The braid 142 is fixed to the catheter shaft 104 distally, but not to the balloon 102. It is in this expanded state of braid 142 and collapsed state of balloon 102 that the braid can act as a stent like structure and allow blood flow to be restored.

Figure 20:
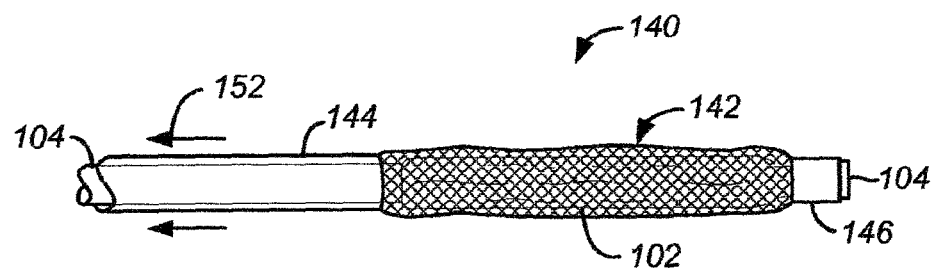

In FIG. 20, by moving the actuator sleeve 144 proximally in the direction of arrows 152, the braid 142 will be contracted against the deflated and collapsed balloon 102, and may even help lower the profile of the collapsed balloon. It is in this contracted state that balloon assembly 140 is typically inserted and removed.

Balloon assembly 140 can be used by itself, that is, not as a replacement for balloon assembly 105 of catheter assembly 100 of FIG. 11. However, by using balloon assembly 140 as a part of catheter assembly 100 additional advantages can be achieved. Four separate but complementary actions can be achieved relative to the inside surface of blood vessel 132 and occlusion 134: 1) It provides a time proven balloon action to effectively dilate the occlusion, 2) It provides a mesh braid over the balloon to more evenly apply stresses on the plaque and thus cause less dissection and injury, 3) The braid, acting independently of the balloon, acts as a transient, removable stent to lessen acute elastic recoil, and 4) When combined with a drug delivery, it will inhibit restenosis. Currently, there are several companies in various stages of development and commercialization of drug eluting balloons. However, these devices do not possess the mechanical advantages provided by many embodiments of the present invention, i.e., the braid to create crevices that allow the plaque to be more homogeneously compressed at lower pressures with less injury, and the ability of the braid to be used as a transient, temporary, or removable stent to reduce the incidence of acute elastic recoil and flow limiting dissections, and acting in concert with the agent to prevent restenosis. Drug eluting and drug coated balloons do indeed provide an advancement over plain old balloon angioplasty (POBA) by lessening the incidence of restenosis from 40-60% to 10-15%. However, restenosis is only one of three major problems associated with POBA. The other two, acute elastic recoil and flow limiting dissections, are not addressed by drug eluting and drug coated balloons. Hence, there will still be a need to place a stent to address these two major problems when they occur, and they occur in up to 40-50% of cases in some studies. In most of these cases, "bail out" or unintended stenting will be needed to address the acute recoil and the flow limiting dissections that occur. The recoil and dissection phenomena are so common that many practitioners actually proceed directly to stenting to save time and complete the intervention with good results rather than attempt to perform just an angioplasty prior to determining the need for stenting. This can add cost to the procedure and leave a metal structure in the patient which may cause other problems such as late stent thrombosis, in-stent restenosis, stent fracture, stent malapposition, and others. These sequalae of the stent placement can often be very difficult to address when they occur. Hence the drug eluting and drug coated balloons are only a partial solution to the dilemma. Utilizing them with the embodiments according to the current invention, however, can provide a complete solution to the three major deficiencies of POBA.

Aspects of the present invention can address all three primary deficiencies of POBA without the need for stenting or foreign materials to be permanently placed within the vessel to maintain a channel for blood flow. Restenosis is addressed, as are drug eluting and drug coated balloons, by providing delivery of a drug or other substance to inhibit restenosis, whether by fluid administration between proximal and distal occluders or via a drug eluting balloon or a drug coated balloon. Many embodiments in accordance with the present invention support the wall of the vessel after dilatation to prevent or severely lessen the occurrence of flow limiting dissections. Many embodiments in accordance with the present invention also support the wall while the drug is acting on the smooth muscle cells to cause them to relax and hence prevents acute elastic recoil. By performing these three actions, the need for stenting will be significantly lessened if not eliminated in most cases. This is not the case when utilizing drug eluting or drug coated balloons without the current invention.

When the temporary scaffold described herein is utilized with a drug coated or drug eluting balloon, the proximal and distal occluders may not be used in at least some cases. The proximal and distal occluders function to contain the liquid drug or substance within a closed space or focal area of the blood vessel. Since the drug or substance is either on the surface of the balloon (drug coated balloon) or within the balloon (drug eluting balloon), there may be no need for the proximal and distal occluders to contain the drug or substance in at least some cases. In this instance, the drug coated or drug eluting balloon may be placed within the braided or stent like structure that comprises the temporary scaffold and used to dilate the lesion similar to the balloon described elsewhere. Alternatively, the lesion may be dilated by a standard POBA balloon beforehand and then the temporary scaffold device comprising the drug eluting or drug coated balloon may be applied subsequently. This may necessitate a catheter exchange, and may not provide some of the advantages of fluid drug or other substance administration in at least some cases, but certainly may be effective.

Because the braid 142 is not attached to the balloon surface, it can act independently of the balloon 102. It is normally expanded with the balloon, but when the balloon is contracted or collapsed to allow for distal blood flow to recommence, the braid can be locked into an expanded configuration by manipulating catheter shaft 104 and actuator sleeve 144 with one's fingers. It is proposed that by leaving the braid expanded for several minutes while blood flow is restored distally, the smooth muscle will accommodate the stretch of the angioplasty. This may well diminish the incidence of acute elastic recoil, one of the major acute problems of POBA. In fact, prolonged expansion of the vessel has just this effect; however, the time that a balloon can be left expanded is limited as ischemia will develop.

The sum of these advantages, i.e., the mechanical advantages of the braid in dilating the plaque with less pressure, less dissection, and less injury along with the temporary stent usage further combined with drug elution to inhibit restenosis can significantly improve patient outcomes.

Many embodiments in accordance with the present invention have the potential to dramatically improve the results of POBA and the potential to improve the results of and replace DES in many cases, especially due to the ability to block the effects of recoil. Such cases include patients with in-stent restenosis, bifurcation lesions, and small vessels lesions. DES will likely remain a dominant strategy in treating many lesions and there will likely always be a need for stenting, atherectomy and other complex treatments; but clearly if feasibility is shown, many embodiments in accordance with the present invention could become the treatment of choice for most angioplasty procedures. In those cases in which it may not achieve optimal results, BMS (or even DES) may then be utilized.

Embodiments according to the present invention may occlude the lumen with a device that will allow the angioplasty catheter shaft 104 to pass through it, and by occluding the distal aspect of the vascular channel to be perfused with the agent, the angioplasty balloon 102 and/or stent delivery balloon assembly 140 may be placed through the proximal occluder catheter shaft 116 and over the support wire 122 of the distal occluder device, the drug infused and the angioplasty and/or stent delivery can take place while the drug is present. This may allow the pressure of the angioplasty balloon 102 and/or stent delivery balloon assembly 140 to force the drug into the vessel wall while the plaque/vessel is being dilated. The drug can be delivered during the procedure and before platelet adhesion would prevent some of the drug from accessing the vessel wall as in the case of existing prior art. The presence of the drug while the action on the plaque or vessel is taking place can deliver more drug to the vessel wall than just passively bathing the vessel after the intervention.

The procedure could take several forms but an exemplary method would be to perform an angiogram to identify the lesion to be treated at the target site 98. After the lesion is identified, a diagnostic catheter may be advanced beyond the occlusion 134 and the distal occluder 124, which is support wire 122 and pull wire 123 based, may be deployed. Distal occluder 124 may essentially comprise a mesh braid covered with an impermeable substance. The diagnostic catheter can be removed and the proximal occluder catheter shaft 116, with proximal occluder 121 at its distal end, can be inserted over the guide wire/distal occluder and the tip of the proximal occluder may be positioned proximal to the lesion. The proximal occluder could be balloon based or non balloon based. There is a mesh braid funnel catheter occluder invented by the current inventor which occludes without the use of a balloon; see U.S. Pat. No. 6,221,006, the disclosure of which is incorporated by reference. The proximal occluder 121 and then the distal occluder 124 may be activated so that compete occlusion of the vascular lumen would be achieved. The blood would be aspirated from the region 109 between the proximal and distal occluders. The agent would be injected as injected agent 111. The agent and its concentration would be determined by the physician. The agent usually would be mixed with contrast so that it would be visible under fluoroscopy. The angioplasty balloon assembly 105 or the stent delivery balloon assembly 140 device or a stent delivery device (not shown) with a BMS or DES would be placed over the support wire 122 of the distal occluder 124 and centered on occlusion 134. The angioplasty or stent delivery can then be performed within this closed system with the agent in place. The angioplasty balloon assembly 105 or stent delivery balloon assembly 140 could then be removed through the proximal occluder 121, and the agent aspirated. The distal occluder 124 would be released and further aspiration done until blood was returned insuring that all of the drug had been aspirated before releasing the proximal occluder. The proximal occluder 121 would then be released, restoring blood flow distally.

Alternatively at this point of the procedure, if a second dilatation was desired, the drug could be aspirated through the proximal occluder after the initial dilatation similar to the above procedure, but before the angioplasty balloon was removed. Similar to above, the distal occluder may be released first while still aspirating. After blood was returned in the aspiration fluid, assuring that the entire amount of drug had been aspirated, the proximal occluder may be released restoring blood flow distally. A second dilatation of the angioplasty balloon could then be performed in a standard conventional manner without any drug being present, the drug having been delivered during the first dilatation.

However, if the desire was to deliver drug during the second dilatation, then the procedure above for the first dilatation may be repeated in a slightly modified manner. There would usually be no need to remove the angioplasty balloon. The proximal occluder would be activated, followed by the distal occluder. The blood could be aspirated and the drug injected through the lumen of the proximal occluder, and around the shaft of the angioplasty balloon. Then, the second angioplasty dilatation could take place, the drug aspirated, the distal occluder released during aspiration, and the proximal occluder released to restore blood flow.

If two separate lesions in the same vascular region needed to be treated, the above may be modified somewhat. After the first lesion was treated as above, the occluders, balloon and temporary balloon stent may be collapsed and moved to a second location where the procedure would be repeated without the laborious step of changing catheters and so on. This would save time and cost, as most balloon catheters cannot be withdrawn and then reinserted into the body as the balloon folds cause reinsertion to be difficult and impractical.

If balloon assembly 140 were utilized in the above procedure instead of a conventional angioplasty balloon, braid 142, acting as a temporary stent, may remain expanded against the vessel wall in a stent like manner during the first balloon inflation, between inflations, during the second balloon inflations and for a chosen period after the last balloon inflation. This action would not only effectively deliver the drug to the vessel wall, but also would provide a temporary stenting effect to the vessel wall to inhibit acute elastic recoil.

Moreover, if balloon assembly 140 were utilized it would provide less injury to the vessel wall by dilating the occlusion at lesser pressures and causing fewer dissections. Therefore, the essence of this procedure is to create less damage to the vessel wall, prevent elastic recoil, compress the plaque efficiently, and to deliver a drug to inhibit intimal hyperplasia as a cause of restenosis.

This procedure has many different ways of being performed as a standard angioplasty balloon, such as balloon 102, may be used, a specialty device, such as a balloon assembly 140, may be used; in addition, stent delivery devices, laser devices, cryoplasty and most any device designed for endovascular treatment of vascular disease may be used in accordance with the present invention. Devices according to many embodiments of the present invention differ from prior art in that a non-balloon distal occluder is preferably used in the procedure. This one step can make it possible to perform the drug perfusion and the intervention in a single step vs. the cumbersome method of having to exchange catheters and then deliver the drug after the fact, or at least after the intervention. While other components of this device are present for the purpose of perfusing drug after angioplasty, the presence of a guide wire (support wire 122) occluder, with any type of proximal occluder that could be traversed by a catheter, can make devices according to many embodiments superior ones as they allow the intervention to be performed while the lesion and vessel wall are being bathed by the drug or other agent. Of course, a balloon occluder may be used distally in the method described above if it contained a shaft thin enough for an inflation channel and means to allow insertion of a treatment device coaxially over the distal occluder shaft, and it is included by this mention as an alternative embodiment.

The one feature of the ability to place the treatment device over the shaft of the distal occluder so that the treatment is conducted concurrently with the drug delivery can be important to the commercial success of the procedure and method of infusing a drug to inhibit restenosis as it can obviate the less than effective method of delivering the drug in a second step in an inefficient manner after the intervention, and with a good deal of pressure upon the vessel wall. Therefore, an aspect of the present invention relates to performing the interventional procedure while the agent is contained within the vascular space. Aspects of the present invention may permit treatment of variable lengths of vessel with the one device vs. the fixed lengths of devices for treating vessels in prior art. If an arterial segment that is stenosed is for example, 1.0 or 2.5 cm in length, then the entire occlusion 134 can typically be treated with a single placement of proximal and distal occluders 121, 124. If the lesion is 25 cm or 50 cm or 100 cm in length, then the same device can be used to treat any of those lesions by varying the length between the proximal occluder and the distal occluder to treat the desired length as the proximal and distal occluders are not connected by a fixed distance as in the prior art. In long lesions, the prior art devices would need to successively move the fixed distance proximal and distal occluders (usually balloons) and provide short overlaps between each segment for multiple segments and multiple treatment sessions. The methods according to many embodiments of the present invention would therefore save time, obviate repeated repositioning of the prior art device and obviate the use of multiple doses of the drug or other substance.

Balloon assembly 140 is inserted into blood vessel 132, positioned at occlusion 134, and the balloon 102 inflated in a standard manner. The inflation of the balloon may expand the braid 142 and this is the usual method of expansion of the braid. More importantly is that the lesion can be dilated successfully, probably with a lesser pressure than a conventional POBA balloon. See FIG. 18. After a first length of time chosen by the operator, typically one or two minutes, the balloon can be deflated while force is exerted on the actuator sleeve in the direction of arrows 150. See FIG. 19. This can keep the braid 142 expanded against the vessel wall while the balloon 102 is contracted allowing for blood flow to be restored distally for a second length of time, usually more than 3 minutes and typically 3 to 90 minutes. The proximal occluder and of the distal occluder can be collapsed after the balloon is deflated to restore flow in the vessel while the braid is expanded against the vessel wall. The balloon inflation may be repeated as many times as desired, and by keeping forward force on the actuator sleeve 144, the braid 142 can remain expanded during, between, and after balloon inflations. There may be a locking mechanism provided so that the forward force can be maintained without manual pressure. Moreover, the temporary stent may be used with modalities other than drugs, such as radiofrequency, electroporation, heat, atherectomy, gene therapy, cryotherapy, electrical currents, radiation, iontophoresis, other pharmacological agents and substances, and the like.

Figure 18:
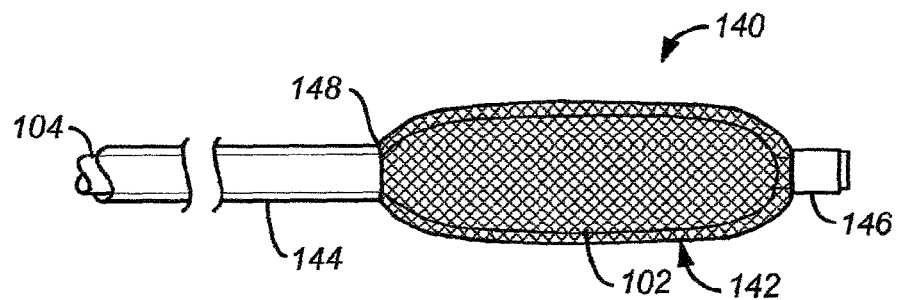

Another alternative configuration of the temporary stent 140 as shown in FIGS. 18, 19, and 20 would be to coat the balloon 102 with an excipient (not shown) that contained a drug such as, but not limited to, paclitaxel, and to use a stent like structure over this specialty balloon as demonstrated in these figures. The stent like structure may or may not be braid, and may be a self expanding stent even. The delivery of the drug directly from the balloon may obviate the need for the proximal and distal occluders previously described as the drug would be delivered from the coated balloon 102 rather than as a fluid within the closed space. Another alternative may be to utilize a porous drug eluting balloon (not shown) instead of the balloon 102 shown in these figures. In this instance, the drug or substance to be delivered may be injected into the porous balloon and delivered from the porous balloon to the vessel wall by a weeping method or the like.

As well a temporary stent could be fitted over the drug coated balloon or drug containing porous balloon as a separate device rather than being fixably attached to the balloon as has been discussed previously.

A temporary stent 140 placed coaxially over the balloon 102 which is not attached to an actuator sleeve 144 as in FIGS. 18-20 can also be an alternative configuration. This stent like structure may be a self expanding non braided stent which would overcome some deficiencies of mesh braid such as poor radial strength, pronounced foreshortening, overlapping thicknesses and the like. It may be braid however. The stent may or may not be attached to the actuator sleeve 144 and the distal catheter 146. If not attached to these, it may be attached to a distal wire described below and at least one wire proximally, or to a combination of wires and actuator sheaths. If utilized with the funnel shaped proximal occluder previously mentioned, the stent structure may be collapsed and retrieved by the combination of forward force on the distal wire, traction force on the proximal wire(s), and by pulling the apparatus into the mouth of the funnel occluder catheter to retrieve it. The use of wires would save precious space by obviating the need for an actuator sleeve which typically would utilize at least 1 Fr. (0.013") in space because of wall thickness.

If a self expanding stent is utilized, it may be mounted over the balloon coaxially and constrained in a compressed configuration inside of a specific delivery device, or even pre-loaded into the lumen of the proximal occluder catheter. In the latter case, the proximal occluder catheter may initially be positioned at the lesion to be treated either primarily or after pre-dilation of the lesion with another angioplasty balloon. Withdrawal of the outer proximal occlusion catheter with forward pressure on the temporary stent apparatus may deliver the temporary stent and balloon apparatus to the site to be treated. The inflation of the balloon may dilate the lesion, the self expanding temporary stent or scaffold may hold the vessel open. Subsequently, the balloon and the temporary stent may be withdrawn into the proximal occlusion catheter or the specific delivery catheter mentioned above.

In even another alternative embodiment, the temporary stent alone may be utilized in a configuration that does not involve a coaxial position over the balloon. The balloon may be used completely separately and not attached to the temporary stent. In other words, the temporary stent may be used subsequently to the balloon dilatation as a planned procedure or a "bail out" procedure because of a flow limiting dissection, recoil, or other reason. In this configuration, the temporary stent may be configured as in FIGS. 18-20 but without the balloon 102. It may be attached to wires as previously discussed or some other means to contract and expand it. However, experiments conducted have shown that it is advantageous to expand a balloon within the closed space containing the drug as the expansion of the balloon creates added pressure within the closed space and essentially drives the drug or other substance into the vessel wall. There is significantly more drug within the vessel wall when done under pressure than when just passively infused into a closed space. The drug also penetrates deeper into the vessel wall with the added pressure than without it and reaches the media and adventitia. In the case of restenosis, the inhibition of smooth muscle cell proliferation and migration in and from the media is of extreme importance. The expansion of the balloon while the drug is present within the closed space will make drug delivery to all levels of the vessel wall more efficient and effective.

To ensure that adequate pressure is achieved within the closed space, a sensor may be placed on the temporary scaffold or either the proximal or distal occluders of the system. Another simple method may be to perform experiments measuring pressures within isolated segments of animals varying the diameter and length of the segment to be isolated and the diameter and length of the expanded balloon, and developing a table of the variables which indicates the volume of fluid needed to achieve the desired pressure within the isolated segment corresponding to a previously determined value. This may obviate the need for an expensive sensor in every device. One of the goals of the current invention is to provide a device which performs several complimentary actions at one time rather than the laborious and time consuming method currently employed of sequentially changing different catheters to perform the separate and different actions desired.

As mentioned above, the scoring of the plaque will typically cause the plaque to compress more evenly and at lower pressures than with POBA. This may be a result of focal areas of force being applied to the plaque with scoring vs. the generally uniform force of a standard angioplasty balloon. Combining the advantageous scoring features with support features of the scaffold can be problematic as scoring demands fewer filaments or members to cut into the plaque and the scaffold demands more filaments or members to add strength to the device. In other words, the number of filaments needed to support the lesion after dilatation can be significantly more than the optimum number of filaments needed to score the lesion. Scoring of the lesion depends on providing a focal force at one or several areas upon and within the plaque. If all of the filaments were scoring filaments, this force may be diluted or divided over all of the filaments and none would be dominant in directing force into the plaque. The force may be generalized rather than being focal, and there would be no area or areas of dominant force to cause the plaque to fracture beneath the scoring elements. Hence only a few scoring filaments are needed to produce the desired results. More filaments would not produce the desired results of a few areas of focal fracturing of the plaque.

If there were only a few filaments for support, the temporary scaffolding would not support the dilated lesion as the strength of the device would be diminished. Hence, there may be a trade-off between the ability to score and the ability to support. This can be solved by an exemplary construction of the temporary scaffold which involves cutting or scoring means and other separate means for supporting the vessel. In other words, there may be specialized members of the temporary scaffold for cutting or scoring and other specialized members for maintaining and supporting the vessel. Other members may be present to prevent dissections even. For example, in the case of braid, the cutting or scoring means may comprise a rectangular or triangular shaped wire, or any shape which has more of a point than a standard round wire for the scoring element. A smaller or larger wire of a different shape than the remainder of the braided structure, or a smaller or larger wire or filament that is of the same shape may be utilized as the cutting or scoring element. These wires or filaments may be directed only in one direction of the braid, and may be interspersed amongst the other braid members. As well, having the larger wires directed in only one direction would conserve valuable space as an overlapping braid creates a situation in which the diameter of the thickest wire is doubled on each side if they were directed in a crossing fashion.

Figure 22:
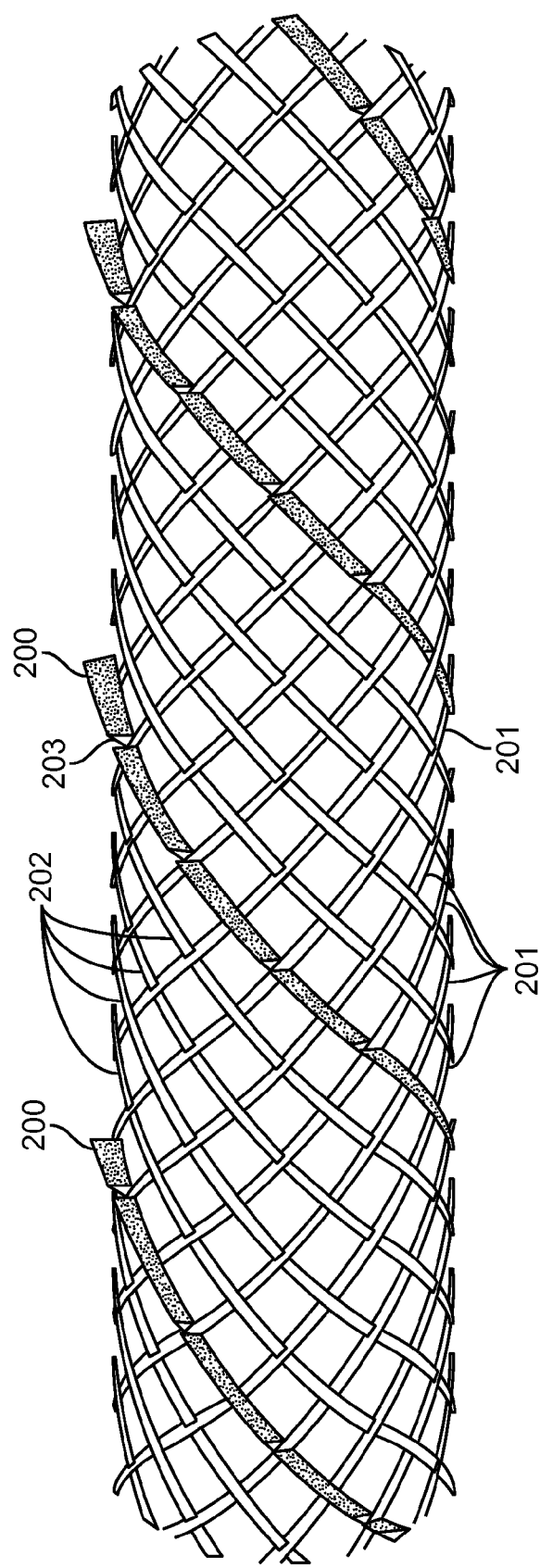
FIG. 22 is a side view of a stent-like temporary scaffold or structure according to many embodiments.

In fact, an exemplary method of obviating the overlapping dilemma is shown in FIG. 22. In this configuration, there are triangular braid filaments 200 directed in one direction spiraling around the tubular braid interposed amongst other braid filaments 202 directed in the same direction and crossing in a braided fashion the remainder of the braid filaments 201 in a different direction. The other braid filaments 201, 202 may be round, flat, rectangular or any shape, but preferably they are lower profile than the triangular braid filaments. In some embodiments, the triangular braid filaments have notches 203 placed to receive the other braid filaments 201 as they cross the triangular filaments 200. Hence these configurations may serve two purposes: 1) It may conserve annular space by eliminating the overlap at the peak of the triangular filament 200 and does not add further to the radial diameter of the braid, and 2) It may preserve the scoring aspect of the apex of the triangle by eliminating the overlap of a braid filament that would inhibit the penetration of the triangular filament into the plaque. Hence a lower profile device can be maintained while enhancing the scoring properties of the device.

The number of cutting or scoring filaments may be from one to several. The fewer cutting or scoring filaments, the more force exerted on the plaque per cutting or scoring filament, hence the more effective at scoring or cutting the device will be. A preferred embodiment would comprise fewer than six scoring or cutting members. Preferably, these scoring or cutting members are oriented in a single direction.

Figure 23:
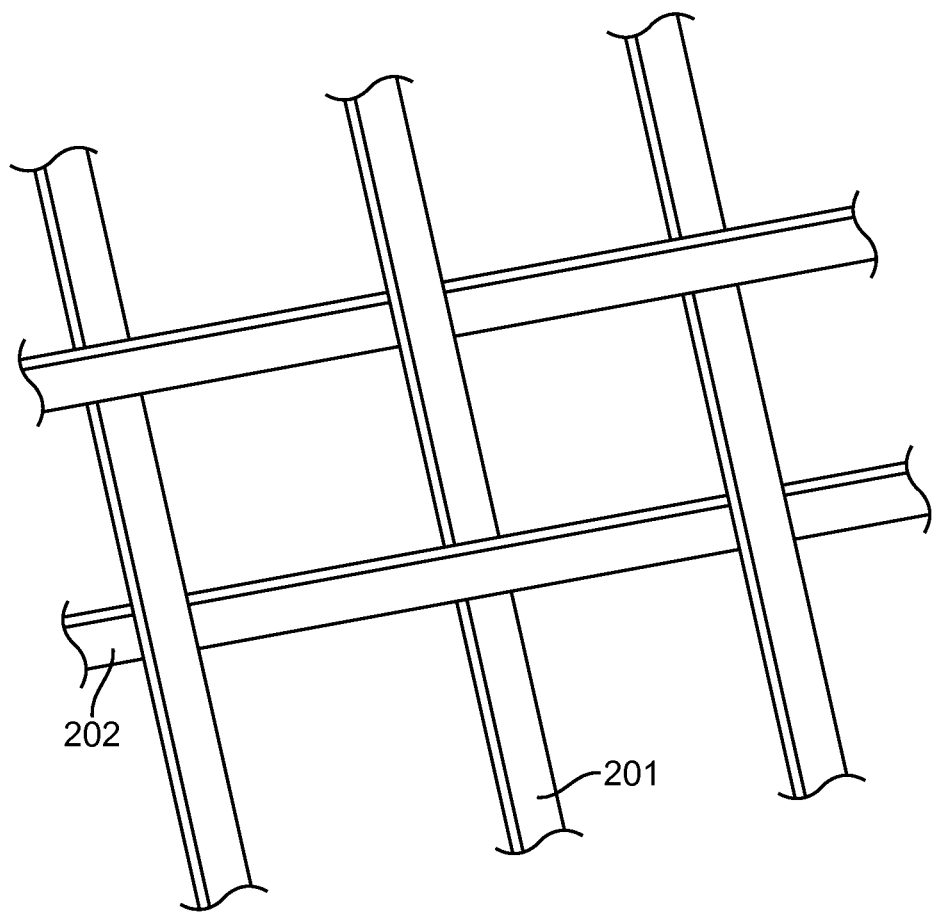
FIG. 23 is a magnified top view of the interwoven filaments of a stent-like temporary scaffold or structure according to many embodiments.
Figure 24:
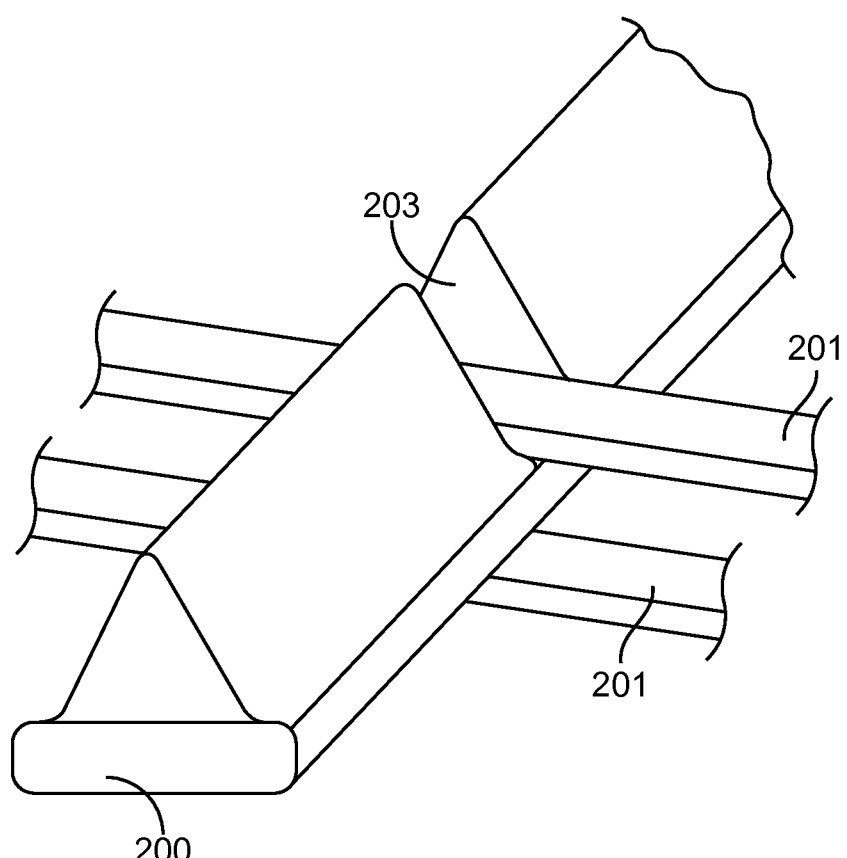
FIG. 24 is a magnified perspective view of non-scoring filaments interwoven and received within a notch of a scoring filament in a stent-like temporary scaffold or structure according to many embodiments.
Figure 25:
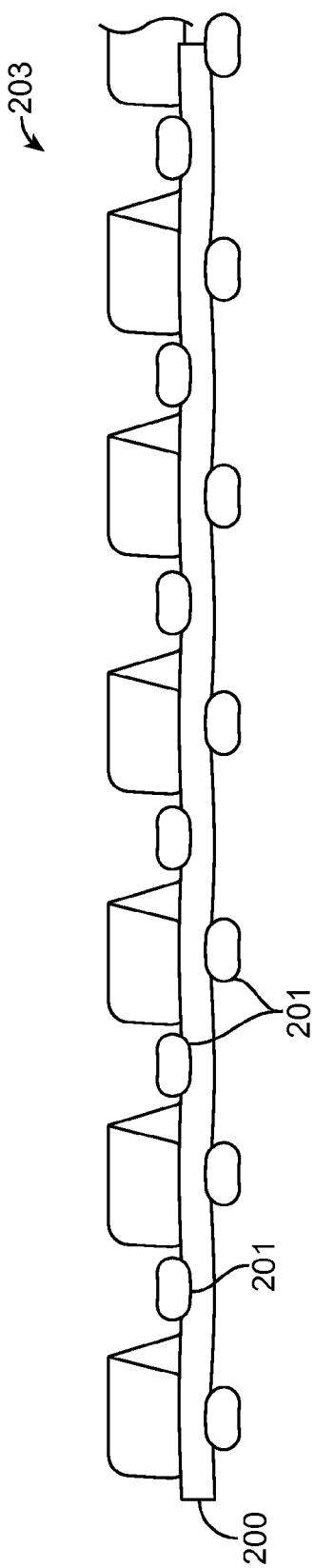
FIG. 25 is a side view of a scoring filament having a plurality of notches for receiving a plurality of non-scoring filaments in a stent-like temporary scaffold or structure according to many embodiments.

FIG. 22 shows an exemplary braid comprising scoring wires 200 and supporting wires 201, 202. FIG. 23 shows expanded view of a section of the braid device containing only the supporting wires 201, 202. The supporting wires or filaments 201, 202, in the case of a braided structure, may be standard round wires or filaments measuring preferably from 0.001" to 0.015" in diameter. They also may be flat, rectangular, or oval, measuring from 0.0005" to 0.010" in thickness and from 0.003" to 0.500" in width. To conserve space, the cutting or scoring wires or members 200 may measure 0.005"

to 0.009" in greatest radial dimension or height to the peak of the triangle, all directed in the same direction and the supportive wires or members 201, 202 measure only 0.001" to 0.005" in greatest radial dimension or height and all directed in the same direction. This may cause the thicker cutting or scoring wires or members to overlap only the thinner supportive wires or members. FIG. 24 demonstrates an expanded section of FIG. 22 in which two rather flat supporting members 201 are interwoven with a scoring member 200. The flat supporting members 201 are present within the notches 203 mentioned above. FIG. 25 demonstrates a section taken along the course of one scoring braid member 200. One can appreciate that the scoring member 200 may cross over, and may be crossed by, the other supporting members 201. FIG. 25 shows that instead of the abrupt notches, there may be rounded indentations or other configurations (not shown) within the scoring members 200 to accommodate the crossing members 201. In fact, a configuration other than shown for illustration purposes in FIG. 25 may be preferable in at least some instances. In fact, it may be preferable to have not notches at all in at least some instances. In this configuration the crossing members would cross the apex of the scoring members (not shown.)

The number of members of the braid will affect the radial strength as well as the pics per inch (the number of wire intersections per inch), the size of the central mandril, the rate of advancement of the mandril as well as other factors. Hence, any number of combinations of the type of wire or filament, shape and dimension of the wire or filament, relative stiffness of the wire or filament, the number of the types of wires or filaments, the total number of wires or filaments, the total number of the structurally important wires or filaments, mandril size, the braid density, the pics per inch, the direction of the thick and thinner members, and other factors are possible and will contribute to the size, strength and functionality of the scaffold. By utilizing this novel technique, one can optimize the cutting or scoring features, the strength of the device, and limit the size, all important goals.

In at least some instances, a particular issue with using a braid as the scaffold is the foreshortening that often occurs when tubular braid is expanded from its elongated configuration in which it has a reduced radial diameter for insertion and removal. When the braid is expanded, either by a balloon as in many embodiments of the present invention or by forcing the two ends of the braid closer to each other, the braid often becomes shorter and there is often movement of the filaments linearly. There is often movement of the filaments in a reverse direction when contracting or collapsing the braid from an expanded position to an elongated configuration with a lesser radial diameter. In such movement, the braid filaments may actually cut into the plaque when expanding. This is not problematic as creating microfractures within the plaque is a goal of the device. However, upon contracting the braid, the elongation of the braid may cause shear forces within the plaque that could tear or disrupt the plaque and lead to deleterious effects such as flaps, dissections, and even extruded fragments of the plaque. Hence, in at least some instances, a majority of the filaments should preferably be rather flat rather than rounded, square, rectangular or other shape that may possess sharp edges that could tear or damage the tissue when moving in a more or less longitudinal direction. Preferably, the rather flat members should comprise rounded edges so that these filaments would have more of a compressive effect rather than a cutting effect on the plaque.

Furthermore to prevent tearing of the plaque or tissue when collapsing the preferred braided structure according to many embodiments of the present invention which has mainly flat members with only a few more or less triangular scoring filaments, a mechanism may be provided so that the outer sleeve of the shaft of the device rotates when being withdrawn. It also may rotate when the balloon is expanding and the braid is foreshortening. Hence, the braid and the scoring filaments may rotate in a spiral manner during foreshortening (expansion) or elongation (collapsing or contracting) of the braid. The spiral motion of the scoring members upon collapsing the braid would cause them to move within the "track" formed by the expansion and the compression of these filaments into the plaque. It may prevent or preclude movement into or through tissue or plaque that had not been scored during expansion and would prevent or preclude damage to the plaque or tissue from the shear forces encountered because of the lengthening or foreshortening of the braid. The rotation or spiral motion of the outer shaft may be controlled by a simple thread and groove arrangement near the proximal end of the outer sheath or at some other location. Other means may be provided to create the desired rotation or spiraling of the scoring fibers upon expansion and contraction.

Figure 26C:
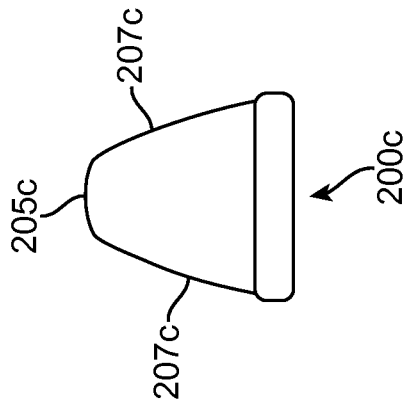
FIGS. 26A to 26C are side views of a plurality of scoring members of a scoring filament in a stent-like structure according to many embodiments.
Figure 26B:
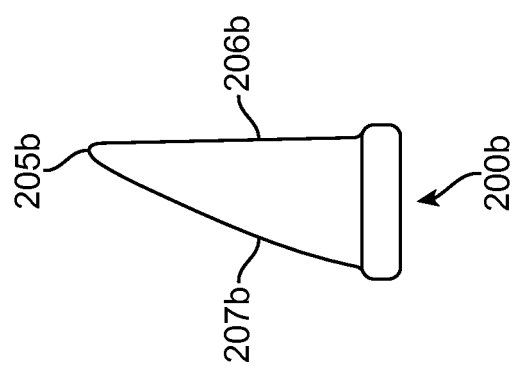
Figure 26A:
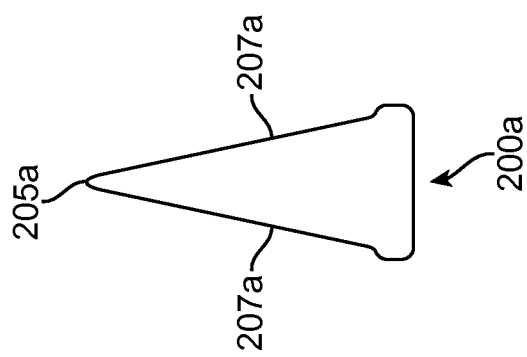

In the discussion above, the scoring member 200 has been referred to as triangular. However, it may be of any shape that scores adequately. In fact, a novel shape is demonstrated in FIG. 26A, which shows a cross section of member 200a. The scoring member 200a in FIG. 26A is triangular with a slightly rounded apex 205a and more or less straight sides 207a. FIG. 26B shows a scoring member 200b with a more or less pointed scoring edge 205b with a more or less straight side 206b and a somewhat rounded side 207b. This would enhance scoring upon expansion as the foreshortening of the braid would cause there to be forward force on abrupt side 206b, and hence scoring of the plaque. Upon contraction of the braid for removal, the somewhat rounded side would more easily be removed from the fissure or scoring tract without tearing the plaque or tissue. FIG. 26C shows a scoring member 200c with a slightly rounded apex 205c and slightly rounded sides 207c. There may be any number of variations that may be used to enhance scoring on one hand and to diminish the damage to the plaque or vessel wall upon collapsing or removing the device on the other hand.

Along these same lines, returning to FIG. 25, another means of enhancing the scoring while limiting the effects of the scoring element on the tissues when contracting or removing the apparatus because of the shear forces caused by the longitudinal movement of the braid may be to heat set at least some of the crossing support members 201 in an "open" position so that they are more or less self expanding. They would be held in a contracted or compressed state by the other non crossing members 202 and the scoring members 200 but also by the proximal traction on the outer sheath 144 of the device. When the balloon is expanded, the braid may expand and the crossing members may be positioned as in FIG. 25 as the pressure from the balloon would drive the scoring members 200 into the plaque and overcome the tendency of the crossing members 201 expand enough to compete with the scoring members 200. When the balloon is relaxed to allow flow while the scaffold is still expanded against the wall, the forward pressure on the outer sheath of the device can keep the scaffold fully expanded and in the same configuration as FIG. 25. However, when the forward pressure on the outer sheath is relaxed, the crossing members may tend to remain expanded as they have been heat set in the open position. The scoring members of the braid may retract and the crossing members may move toward the apex of the scoring members as the braid contracts further essentially shielding the apex of the scoring members from the surrounding plaque and tissue, hence limiting tearing of the plaque and tissue by the scoring member. This action of outward pressure of the crossing members 201 while the scoring members are contracting may urge the tissue within the notches to be expressed from the notches, at least before the entire braid is put into severe tension by traction of the outer sheath relative to the inner sheath. The crossing members 201 of FIG. 25 also are beneath the scoring members 200 as well as within the notches 203. Hence there may be some competition from this position to keep the scoring members from relaxing properly and to inhibit the action described in this paragraph. The crossing members however may not effect or have minimal effect on the position of the scoring members which have much more mass. Within the notches, they would only maintain their position while the scoring members retract. Most of the members of the braid are flat, hence the shear forces caused by collapsing the braid and the resulting longitudinal movement of the braid will be minimized by these non scoring support members that will compress the tissue rather than score it. Hence the overall design of the device with the vast majority of the members being of a flat atraumatic design may protect the plaque and tissues from the shear forces created from collapsing and removing the braid.

In the case of a non braided scaffold, including a laser cut scaffold, some of the struts of the scaffold may be constructed so that while most all of struts are more or less configured in a cylindrical orientation when the device is contracted or collapsed for insertion, that upon expansion some part of the struts or some of the struts may be oriented more or less perpendicular to the vessel wall. These more or less perpendicular struts, or members of the stent, will act as a scoring element when compressed into the plaque by the expansion of the balloon against the stent or just by the self expanding action of the stent in the case of a self expanding stent. When contracted or compressed for removal, these struts or parts of the struts may return to the more or less cylindrical shape. Other struts or parts of struts may be consistently oriented in a conventional cylindrical pattern to provide strength to the scaffold.

Further embodiments of the present invention that combine the features of the system would be to utilize the proximal occluder as the delivery vehicle for the self expanding temporary scoring scaffold. Instead of a separate outer tube constraining the self expanding temporary scoring scaffold, it may be placed within the proximal occluder which would constrain it before delivery. To deploy the self expanding temporary scoring scaffold, the proximal occluder catheter may be placed just distal to the lesion to be dilated or treated, and the inner catheter attached to the self expanding temporary scoring scaffold would be held in place while the proximal occluder catheter is withdrawn albeit with the occlusion portion of the device in a contracted or non occlusive configuration. Once the lesion is covered by the self expanding temporary scoring scaffold, the proximal and distal occluders may be deployed, the agent injected, and the lesion dilated, preferably with a balloon. Subsequently, the self expanding temporary scaffold would be left expanded and the balloon collapsed along with the proximal and distal occluders to restore blood flow. After several minutes to hours, the self expanding temporary scaffold would be recovered into the proximal occluder or some other specific delivery/recovery device.

Figure 27A:
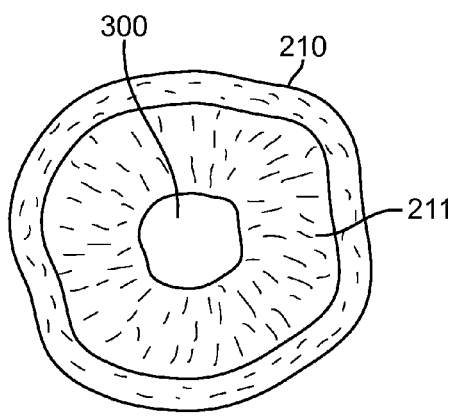
FIG. 27A is a cross-sectional view of an occluded blood vessel prior to treatment in accordance with many embodiments.
Figure 27B:
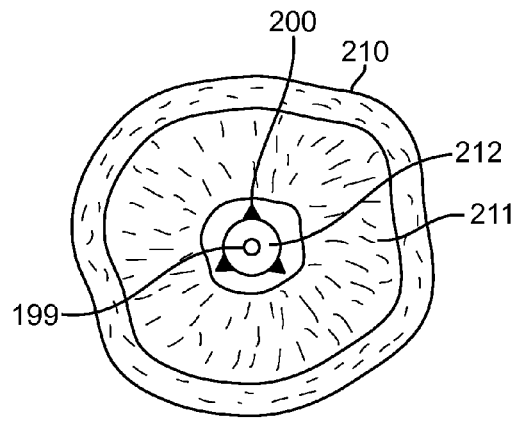
FIG. 27B-27D are cross-sectional views of a stent-like temporary scaffold or structure disposed over an expandable element as used to treat the blood vessel occlusion of FIG. 27A in accordance with many embodiments.

FIG. 27A-E show cross sections of a blood vessel 210 with partially occluding plaque 211 and a vessel lumen 300. FIG. 27A shows the blood vessel 210 with the occluding plaque and the vessel lumen 300 alone. FIG. 27B demonstrates the non expanded balloon 212 and scaffold 213 may be indistinguishable from each other as they are immediately adjacent to one another, catheter shaft 199 and with the scoring members 200 of the scaffold 213 within the existing lumen 300 of the vessel 210. This configuration may generally correspond to FIG. 16 which is a longitudinal section of a non expanded interventional balloon device 102.

Figure 27C:
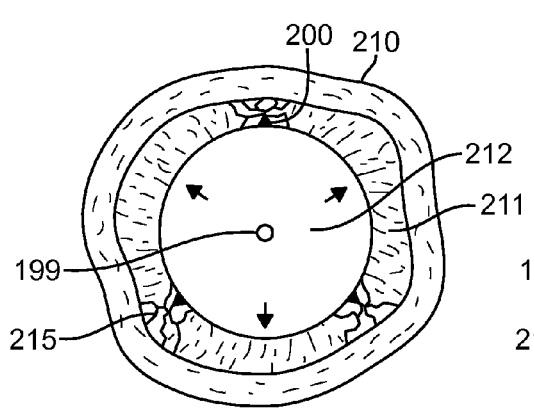

FIG. 27C demonstrates the balloon 212 and scaffold 213 partially expanded which can cause the scoring members 200 to create microfractures 215 with the plaque 211. The drug or substance may be present during this expansion if a fluid drug is utilized with the proximal and distal occluders as discussed elsewhere. Alternatively or in combination, the drug or substance may be delivered via a drug coated balloon 212 at this time if it is to be delivered in that manner. Usually delivery by a drug eluting or drug weeping balloon 212 will be done before or subsequent to this action, if that modality is utilized, as the drug eluting balloon 212 may not have enough radial force to distend the lesion adequately in at least some cases.

Normally, expansion by an angioplasty balloon would produce uncontrolled and random dissections in the plaque. These microfractures produced by the scoring elements 200 of the temporary scaffold 213 produce smaller focal and controlled dissections of the plaque which may result in fewer flow limiting dissections that may demand the subsequent placement of permanent stents. Also, the supporting elements of the temporary scaffold 213 will hold the compressed plaque and pieces of the compressed plaque against the vessel wall and prevent parts of the plaque and other tissue from protruding into the lumen and producing a flow limiting dissection. Moreover, the microfractures serve as conduits or crevasses for the drug or substance to access the vessel wall where they may act upon the smooth muscle cells to cause the smooth muscle cells to relax and prevent the smooth muscle contraction that causes acute elastic recoil. Action of the drug or substance on the smooth muscle cells also may result in a significant decrease in restenosis subsequently as well. The controlled dissections and microfractures from this scoring aspect may cause less injury to the vessel wall which also may result in fewer incidences of recoil, flow limiting dissections, and restenosis even without the drug or substance. The combination of the mechanical features of the current invention and the pharmaceutical component are often complementary. The mechanical features may limit the recoil, dissections and restenosis without the drug, but addition of the drug may improve the results even more.

Figure 27D:
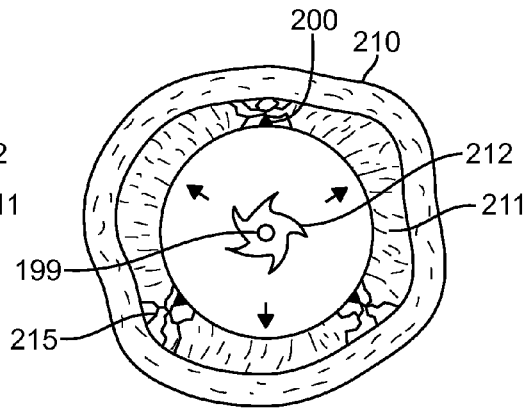

FIG. 27D demonstrates the balloon 212 to be deflated after having compressed the plaque and the scaffold against the plaque 211 compressed and the microfractures 215 extending further into the plaque 211. At this point, the scaffold 213 can be left expanded preferably for at least several minutes to support the dilatation of the plaque 211 and to prevent recoil and dissections. The arrows demonstrate the outward pressure to support the plaque and prevent recoil or flaps from dissections from obstructing or limiting flow.

The leaves of the balloon 212 are collapsed and the balloon 212 is refolded after it has been deflated.

Figure 27E:
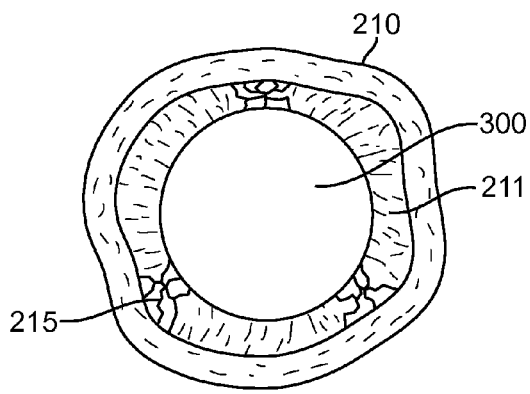
FIG. 27E is a cross-sectional view of the occluded blood vessel of FIG. 27A after the treatment of FIGS. 27B-27D in accordance with many embodiments.

FIG. 27E demonstrates the balloon 212 and scaffold 213 to have been removed leaving the dilated plaque 211 compressed against the arterial wall 210. Elastic recoil which occurs quite frequently has been prevented by the simultaneous administration of the drug or substance while supporting the compressed plaque and arterial wall with the temporary scaffold. Flow limiting dissections may be avoided because of the support of the arterial wall by the temporary scaffold. The drug or substance that has been administered may prevent, or significantly lessen, restenosis. Hence, there is often no need for a stent to be used as the problems solved by stent placement may have been addressed by the use of the devices and methods in accordance with many embodiments of the current invention.

Combining the elements of many embodiments, including the temporary stent to dilate the lesion at a lesser pressure with less injury to the wall and to be utilized to reduce or eliminate elastic recoil along with one or more of the other modalities, may reduce or eliminate the need for the administration of a drug agent to inhibit restenosis. However, combining the drug administration with another modality listed above and the temporary stent element may even further solve many of the short and long term sequelae of vascular intervention, and may even further eliminate the need for stenting or surgery in many cases. If the dilatation of the lesion was adequate because of the proven effect of the typically wire-like temporary stent exterior to the balloon being able to dilate plaque more effectively than POBA, if the lesion was held open by the temporary stent while the drug acts upon the smooth muscle cells and to relax them preventing elastic recoil, and another modality from the list above, for example electroporation, was utilized to enhance the absorption of the drug and to act on the cells of the vascular wall independently to further inhibit restenosis, then all of the reasons to use conventional, non-temporary stents would be obviated. The problems that stents solve may be eliminated. There may be no reason to use a stent in many cases, and this would benefit the patient and the healthcare system. Stents are not only costly, but have long term negative consequences, including in-stent restenosis, late stent thrombosis, and the need to be placed on expensive and potentially deleterious drugs for extended periods.

Figure 21:
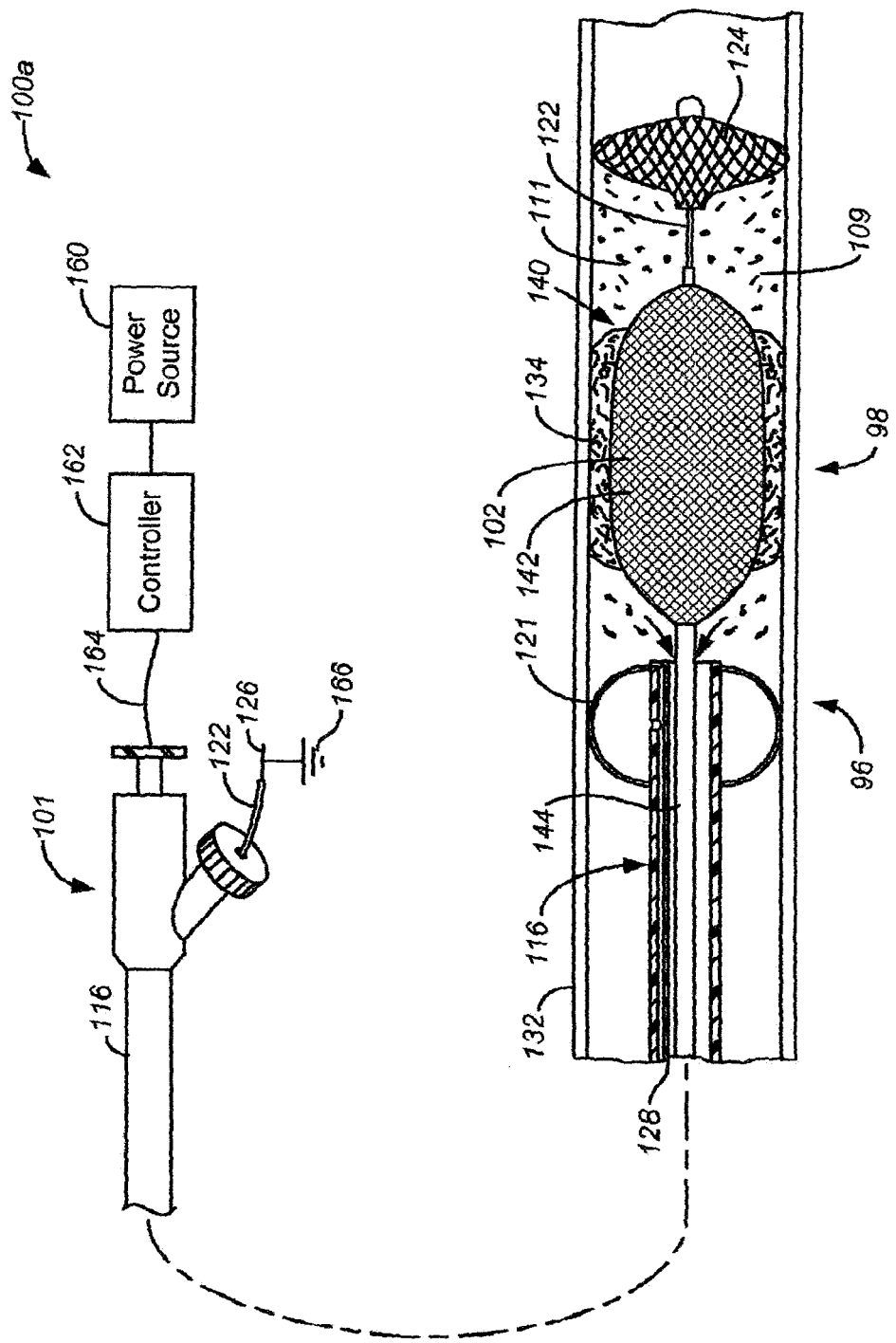
FIG. 21 is a side view, in partial cross-sectional, of an electroporation catheter assembly similar to the examples of FIGS. 11 and 18.

In the case of electroporation, and some of the other modalities, an electrically conductive temporary stent may be used to transfer the energy or electrical pulses to the vessel wall. FIG. 21 illustrates an electroporation catheter assembly 100a constructed to permit the application of electric current to the wall of blood vessel 132 to create transient pores in the cell membrane through which, for example, a drug may pass. Braid 142, acting as a temporary stent, is connected to an external power source 160 and a computer-based controller 162 by wires 164 within the wall of external actuator sleeve 144. Controller 162 would be utilized to program the pulse duration, sequence, amplitude, voltage, amperage, and other parameters to deliver the prescribed energy or electrical pulses to the vessel wall through the temporary stent. It may also be utilized to ascertain electrical impedance or other feedback parameters so that the proper energy parameters may be programmed or prescribed. In this example actuator 126 electrically connects distal occluder 124 to ground 166 thereby grounding the vessel wall. Alternatively or in combination, the energy, such as in the form of electrical pulses, may be delivered through a configuration other than the temporary stent. The electroporation may be used to facilitate the delivery of a drug, but also may be used alone to create the pores in the wall of the cell without the drug being present. The cell is then unable to recover from having these pores in the wall, and it eventually dies, in effect a type of accelerated apoptosis. Adding the additional modality to the system of occlusion elements, drug infusion, dilatation and temporary stenting described herein would add very little incremental cost, but may be necessary to reduce the restenosis rate under the 10% rate expected from the above system without the additional modality.

Paclitaxel acts on the cytoskeleton or microtubules within smooth muscle cells by enhancing polymerization and causes the smooth muscle cells to relax. There are other cellular effects, certainly, but the dysfunctional microtubules are thought to be reason the smooth muscle cell relaxes rather than contracts as a result to exposure to certain drugs. The temporary stent created by braid 142 combined with paclitaxel should provide enough time of prolonged distension of the vessel for the paclitaxel to act upon the cytoskeleton and microtubules so that the smooth muscle cells would not contract upon the removal of the temporary stent. Many embodiments of the present invention may take advantage of paclitaxel or other antiproliferative drug through the use of the braid 142 (or other stent structure) acting as a temporary stent to provide this action of prolonged expansion, allowing the drug to act upon the cells so that they will not contract when the temporary stent is removed. Without the prolonged expansion, the drug would likely not have enough time to act upon the cellular components to cause the smooth muscle cell to relax. The extra time provided by the expanded temporary stent while blood is flowing through the area along with the uptake and action of the drug will likely result in diminished elastic recoil of the vessel, and better long term patency.

Many embodiments of the present invention also provide a method of infusing an antiproliferative drug or other agent that acts upon the smooth muscle cells and structures within the arterial wall and prolonging the distension of the vessel with a balloon, a temporary stent or scaffolding, or other structure to reduce the incidence of elastic recoil, restenosis, and/or other effects of the intervention.

In one example, the above method may entail placing the proximal and distal occluders on each side of the lesion to create an isolated region, activating the proximal and distal occluders, injecting the drug, performing the therapeutic angioplasty intervention with a temporary stent device as has been described leaving the temporary stent expanded against the vessel wall, deflating the angioplasty balloon so blood flow could be restored subsequently, aspirating the drug along with other flowable material (or even removing it from the isolated region by releasing it downstream), deactivating the proximal and distal occluders, and removing the distal occluder. This may restore flow in the vessel, and the temporary stent would still maintain annular pressure against the vessel wall to prevent elastic recoil while the drug, having been absorbed by the smooth muscle cells, can act upon the microtubules of those smooth muscle cells to create a relaxation of these smooth muscle cells and prevent acute elastic recoil. In some embodiments, the drug or other agent may be allowed to contact the target site for a period of time, such as from 30 seconds to 20 minutes, before the therapeutic angioplasty intervention, or other pressure applying step, is performed. In some embodiments, the angioplasty balloon, or other pressure applying apparatus, can be used to apply pressure to the vessel wall from about one minute to five days. When the balloon is left in place for extended periods, it is usually in a collapsed state to permit blood flow around it. It is expanded only when necessary, such as to expand the lesion during angioplasty and to expand the temporary stent.

Alternatively, the above example may be modified so that instead of a temporary stent, a plain angioplasty balloon device, a stent, such as a bare metal stent or a bioresorbable or biodegradable stent which is intended not to be removed, atherectomy, or other therapeutic device is utilized. Also, the deactivated proximal and distal occluders may be left in place within the vessel while a pressure device is providing force against the vessel wall, and removed when the pressure device is removed. The temporary stent or other pressure device would typically remain in place for at least several minutes and at most for several hours to days to prevent elastic recoil. If, for example, the balloon assembly 140 of FIG. 20 is left in place for several days, balloon 102 is collapsed permit blood flow around it. In such a procedure heparin or some other agent could also be administered.

Moreover, the temporary stent may be used with other modalities other than drugs, such as radiofrequency, electroporation, heat, atherectomy, gene therapy, cryotherapy, electrical currents, radiation, iontophoresis, other pharmacological agents and substances, and the like.

Other variations of temporary stenting, can be used. For example, the braid 142 may be contracted by guide wire(s) instead of the actuator sleeve 144. The braid may be contracted by moving the distal part of the braid more distally by using an engagement device instead of an actuator sheath. In other words, if the distal aspect of the braid was engaged or attached to the distal aspect of the guide wire rather than fixed to the distal aspect of the balloon catheter as described in the preferred embodiments, then moving the guide wire distally would collapse the braid and moving the guide wire proximally would expand the braid, or at least maintain expansive pressure upon the already expanded braid.

Aspects of the present invention differ significantly from the Ya patent discussed above in that no dissolving agent outflow bores are used, the focus is not directed to dissolving a thrombus, and any antiproliferative agent is injected before the intervention and is present during the therapeutic intervention, not removed before the intervention as in Ya. Any subsequent intervention or therapy (angioplasty, stent placement, and the like) are performed after the removal of the dissolved thrombus in Ya. Moreover, the thrombus dissolving agent and the dissolved thrombus must be removed in the method of Ya, which is aimed at removing a thrombus, whereas there is typically no need to remove any antiproliferative agent when practicing the present invention. The dose of the antiproliferative agent is much lower than the systemic dose administered a patient receiving chemotherapy for treatment of a tumor.

In most embodiments disclosed in the Zadno-Azizi reference discussed above, the device is comprised of two distinct lumens, an irrigation pathway and an aspiration pathway, much different from the device and method of the current invention. In the single example disclosed in Zadno-Azizi in which there is only a single aspiration path, the therapy catheter must be removed for the device to function. In contrast with many embodiments of the present invention, it is preferable to leave the therapy device in place even if the injected substance is to be removed. In many cases, there is no need to remove any antiproliferative agent used with the present invention, again a distinction from the method of Zadno-Azizi. The fluid containing the embolic material must be withdrawn for the Zadno-Azizi to be effective less the embolic material embolizes downstream. The success of the many embodiments of the present invention is not predicated on removal of any injected drug, as the drug may be released downstream where it likely would be harmless to the tissues.

Even more important in distinguishing from the method of Zadno-Azizi is the timing aspect. The fluid injected and aspirated is done after the therapeutic invention with the Zadno-Azizi method whereas in accordance with many embodiments of the present invention an agent to inhibit restenosis, such as, but not limited to paclitaxel, is used—the agent may be injected before the therapeutic procedure and left in place during the therapeutic procedure. The antiproliferative agent may or may not be aspirated subsequent to the therapeutic procedure.

Moreover, the prior art devices of Ya and Zadno-Azizi both use a distal occluder with a hollow lumen, which is needed to inflate the distal balloon. Many embodiments of the present invention have no need for this feature when the distal occluder is a mechanical blocking element so that they are in no need for a hollow lumen along the distal occluder.

The balloon stent assembly according to many embodiments of the present invention, in contrast with known temporary stents, will both dilate the plaque in a controlled manner using the balloon, which causes little injury to the vessel, and support the vessel for an extended period of time using the temporary stent. Known temporary stents are commonly intended to only support the vessel after something untoward happens during the procedure, i.e., dissection, vasospasm, or vasoconstriction. Many embodiments of the present invention, because all of the functions (dilatation and support functions) happen more or less simultaneously, prevent noticeable dissections, vasospasm, or vasoconstriction as the vessel wall is supported during and immediately after the intervention, a great improvement over the prior art device. There is often virtually no time for the untoward events to occur with the current invention as there is no time that the vessel wall does not have radial force being exerted upon it. Moreover, many embodiments of the present invention will prevent acute elastic recoil which may be due to many other factors other than dissection, vasospasm, or vasoconstriction.

In the case of an iatrogenically caused dissection from POBA, guide wire passage, atherectomy, or instrumentation of any of many kinds, the temporary stent may be used to "tack down" the flap from the dissection, and to improve the appearance of the vessel by expanding the temporary stent against the vessel wall, deflating the balloon and leaving the temporary stent expanded for several minutes to an hour or so, while providing for blood flow through the area of interest.

In the case of spontaneous dissections, as in the aorta, the temporary stent may be utilized as a temporizing measure to direct blood flow into the true lumen while the interventionalist is deciding on which particular stent graft to use and preparing for the insertion of a stent graft. As well, in cases of aortic aneurismal rupture, the temporary stent may be used before the definitive treatment to stop the hemorrhage and stabilize the patient. In these cases, the temporary stent may or may not have an elastomer or other material covering the part that contacts the vessel wall.

The above descriptions may have used terms above, below, top, bottom, over, under, et cetera. These terms may be used in the description and claims to aid understanding of the invention and not used in a limiting sense.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medical device for treating a target site in a body lumen, the medical device comprising:
   a stent-like structure comprising a plurality of scoring filaments and a plurality of scoring filaments and a plurality of non-scoring filaments interwoven with one another such that the plurality of scoring filaments cross over and under the plurality of non-scoring filaments, each scoring filament and non-scoring filament extending continuously over a full length of the stent-like structure, wherein the stent-like structure comprises more non-scoring filaments crossing over and under scoring filaments than scoring filaments cross over and under non-scoring filaments, wherein each scoring filament has a shape providing a scoring element, wherein the plurality of non-scoring filaments are configured to radially support the body lumen after the stent-like structure has been expanded therein, and wherein the shape of each scoring filament provides a plurality of notches, each notch receiving an individual non-scoring filament as the non-scoring filament crosses over the scoring filament.

2. The medical device of claim 1, wherein the stent-like structure comprises a tubular mesh braid.

3. The medical device of claim 1, wherein the stent-like structure has an expanded configuration and a collapsed configuration, and wherein the stent-like structure in the expanded configuration is collapsible into the collapsed configuration.

4. The medical device of claim 3, wherein the stent-like structure in the expandable configuration is collapsible into the collapsed configuration by axially shortening the stent-like structure.

5. The medical device of claim 1, wherein one or more of the plurality of scoring filaments or the plurality of non-scoring filaments are non-axial.

6. The medical device of claim 5, wherein one or more of the plurality of scoring filaments or the plurality of non-scoring filaments are helically wound over a longitudinal axis of the stent-like structure.

7. The medical device of claim 6, wherein one or more of the plurality of scoring filaments or the plurality of non-scoring filaments are helically wound in the same direction.

8. The medical device of claim 5, wherein the plurality of scoring filaments are helically wound over a longitudinal axis of the stent-like structure.

9. The medical device of claim 8, wherein the plurality of scoring filaments are helically wound in the same direction.

10. The medical device of claim 1, wherein a cross-section of each scoring filament has one or more of a pointed, triangular, or rectangular shape.

11. The medical device of claim 1, wherein a cross-section of each non-scoring filament has one or more of a flat, rounded, rectangular, or cylindrical shape.

12. The medical device of claim 1, further comprising an expandable element, wherein the stent-like structure is disposed over the expandable element, and wherein the expandable element is expandable to urge the stent-like structure radially outward against an inner wall of the body lumen.

13. The medical device of claim 12, wherein the expandable element comprises an inflatable balloon.

14. The medical device of claim 12, wherein the expandable element is independently collapsible from the stent-like structure.

15. The medical device of claim 12, wherein the expandable element comprises an outer surface coated with a therapeutic agent or substance.

16. The medical device of claim 12, wherein the expandable element comprises one or more pores for releasing a therapeutic agent or substance.

17. The medical device of claim 12, further comprising a catheter shaft, wherein the expandable element is disposed over the catheter shaft.

18. The medical device of claim 17, further comprising an expandable proximal occluder disposed over the catheter shaft proximal of the expandable element and the stent-like structure.

19. The medical device of claim 17, further comprising an expandable distal occluder.

20. The medical device of claim 19, wherein the distal occluder is advancable through an inner lumen of the catheter shaft to be positioned distal of the expandable element and the stent-like structure.

21. The medical device of claim 19, wherein the distal occluder is non-inflatable.

22. The medical device of claim 1, wherein the full length of the stent-like structure extends from a proximal end of the stent-like structure to a distal end of the stent-like structure.

23. The medical device of claim 1, wherein the full length of an individual scoring filament extends from a proximal end of the stent-like structure to a distal end of the stent-like structure.

24. A medical device for treating a target site in a body lumen, the medical device comprising:
    a stent-like structure comprising a plurality of scoring filaments and a plurality of non-scoring filaments interwoven with one another, each scoring filament and non-scoring filament extending continuously over a full length of the stent-like structure,
    wherein each scoring filament has a shape providing a scoring element, and
    wherein the shape of each scoring filament provides a plurality of notches, each notch defined by an indentation in the scoring element, and each individual non-scoring filament being received in and slidable over a corresponding individual notch as the stent-like structure expands or contracts.

25. The medical device of claim 24, wherein the stent-like structure comprises a tubular mesh braid.

26. The medical device of claim 24, wherein the plurality of non-scoring filaments are configured to radially support the body lumen after the stent-like structure has been expanded therein.

27. The medical device of claim 24, wherein the stent-like structure has an expanded configuration and a collapsed configuration, and wherein the stent-like structure in the expanded configuration is collapsible into the collapsed configuration.

28. The medical device of claim 27, wherein the stent-like structure in the expandable configuration is collapsible into the collapsed configuration by axially shortening the stent-like structure.

29. The medical device of claim 24, wherein one or more of the plurality of scoring filaments or the plurality of non-scoring filaments are non-axial.

30. The medical device of claim 29, wherein one or more of the plurality of scoring filaments or the plurality of non-scoring filaments are helically wound over a longitudinal axis of the stent-like structure.

31. The medical device of claim 30, wherein one or more of the plurality of scoring filaments or the plurality of non-scoring filaments are helically wound in the same direction.

32. The medical device of claim 24, wherein a cross-section of each scoring filament has one or more of a pointed, triangular, or rectangular shape.

33. The medical device of claim 24, wherein a cross-section of each non-scoring filament has one or more of a flat, rounded, rectangular, or cylindrical shape.

34. The medical device of claim 24, further comprising an expandable element, wherein the stent-like structure is disposed over the expandable element, and wherein the expandable element is expandable to urge the stent-like structure radially outward against an inner wall of the body lumen.

35. The medical device of claim 24, wherein the plurality of scoring filaments and the plurality of non-scoring filaments are interwoven with one another such that the plurality of scoring filaments cross over and under the plurality of non-scoring filaments.

\* \* \* \* \*